US008314064B2

(12) United States Patent
Watkins et al.

(10) Patent No.: US 8,314,064 B2
(45) Date of Patent: Nov. 20, 2012

(54) URIDINE ADMINISTRATION STIMULATES MEMBRANE PRODUCTION

(75) Inventors: Carol Watkins, Cambridge, MA (US); Richard J. Wurtman, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/972,777

(22) Filed: Oct. 26, 2004

(65) Prior Publication Data

US 2005/0176676 A1 Aug. 11, 2005

Related U.S. Application Data

(63) Continuation-in-part of application No. 10/941,025, filed on Sep. 15, 2004, which is a continuation-in-part of application No. 09/363,748, filed on Jul. 30, 1999, now Pat. No. 6,989,376.

(60) Provisional application No. 60/095,002, filed on Jul. 31, 1998.

(51) Int. Cl.
*A61K 31/70* (2006.01)
*A61K 38/18* (2006.01)
*C07K 14/48* (2006.01)

(52) U.S. Cl. .............................. 514/8.4; 514/50; 514/51

(58) Field of Classification Search .................... 514/50, 514/51
See application file for complete search history.

(56) References Cited

U.S. PATENT DOCUMENTS

| | | | |
|---|---|---|---|
| 4,221,784 A | 9/1980 | Growdon et al. | |
| 4,609,647 A | 9/1986 | Growdon et al. | |
| 4,960,759 A | 10/1990 | De Luca et al. | |
| 5,141,943 A | 8/1992 | Naguib et al. | |
| 5,470,838 A * | 11/1995 | von Borstel et al. | 514/50 |
| 5,567,689 A | 10/1996 | Sommadossi et al. | |
| 5,583,117 A * | 12/1996 | von Borstel et al. | 514/50 |
| 5,601,829 A | 2/1997 | Quintanilla Almagro et al. | |
| 5,723,449 A | 3/1998 | Sommadossi et al. | |
| 5,962,459 A * | 10/1999 | Piazza et al. | 514/269 |
| 6,191,154 B1 | 2/2001 | Landreth et al. | |
| 6,258,795 B1* | 7/2001 | von Borstel et al. | 514/49 |
| 6,274,563 B1* | 8/2001 | von Borstel et al. | 514/50 |
| 6,316,426 B1* | 11/2001 | von Borstel et al. | 514/50 |
| 6,472,378 B2* | 10/2002 | von Borstel | 514/50 |
| 6,989,376 B2* | 1/2006 | Watkins et al. | 514/50 |
| 7,105,498 B2* | 9/2006 | von Borstel et al. | 514/49 |
| 2001/0005719 A1* | 6/2001 | Von Borstel | 514/49 |
| 2002/0028787 A1 | 3/2002 | Watkins et al. | |
| 2003/0114415 A1* | 6/2003 | Wurtman et al. | 514/51 |

FOREIGN PATENT DOCUMENTS

| | | |
|---|---|---|
| DE | 2508474 | 9/1976 |
| DE | 2629845 | 1/1978 |
| EP | 178267 A2 * | 4/1986 |
| EP | 0178267 A2 * | 4/1986 |
| EP | 0 348 360 | 12/1989 |
| EP | 0 462 075 | 12/1991 |
| JP | 07/215879 A * | 8/1995 |
| JP | 09/30976 A2 * | 2/1997 |
| JP | 2001/233776 A2 * | 8/2001 |
| JP | 2001/233776 A2 * | 8/2004 |
| RU | 2003332 C1 | 11/1993 |
| WO | WO89/03837 A1 * | 5/1989 |
| WO | WO 89/03837 A1 * | 5/1989 |
| WO | WO 95/05180 | 2/1995 |
| WO | WO 97/43899 A1 * | 11/1997 |
| WO | WO97/43899 A1 * | 11/1997 |
| WO | WO97/45127 A1 * | 12/1997 |
| WO | WO 97/45127 A1 * | 12/1997 |
| WO | WO 00/06174 | 2/2000 |
| WO | WO 00/11952 | 3/2000 |
| WO | WO 00/50043 A1 * | 8/2000 |
| WO | WO00/50043 A1 * | 8/2000 |
| WO | WO 2005/079250 A2 | 9/2005 |
| WO | WO 2005/112635 A | 12/2005 |
| WO | WO 2006/031683 | 3/2006 |
| WO | WO 2006/127620 | 11/2006 |

OTHER PUBLICATIONS

Merlini et al., "Effects of Large Doses of Pyrimidine Nucleosides Cytidine and Uridine in Elderly Patients with Neuropsychological Disturbances Caused by Vascular and Cerebral Metabolic Insufficiency," Gazzetta Medica Italiana Archivio Scienze Medic.*
Gallai et al. (II), "Multi-Infarct Dementia: Modification of the P300 Cognitive Event-Related Potential in Patients Treated with the Association of Cytidine and Uridine," Rivista di Neuropsichiatria e Scienze Affini, 41(1), 1-9 (1995); BIOSIS, 1996, Ab.*
Manna et al., "Effects of Short-Term Administration of Cytidine, Uridine and L-Glutamine Alone or in Combination on the Cerebral Electrical Activity of Patients with Chronic Cerebrovascular Disease," Intl. Journal Clinical Pharmacology Research, 8(3).*
Keilbaugh et al., "Anti-Human Immunodeficiency Virus Type 1 Therapy and Peripheral Neuropathy: Prevention of 2' 3'Dideoxycytidine Toxicity in PC12 Cells, a Neuronal Model, by Uridine and Pyruvate," Molecular Pharamcology, 44(4), 702-706 (Oct. 1, 19.*
Ingraham et al., "Nucleoside Diphosphokinase from Salmonella typhimurium," Chapter 48 in Methods in Enzymology, LI(vol. 51), Hoffee et al. (eds.), New York, NY, 1978, Academic Press, only pp. 371 and 375 supplied; assorted portions of other chapter.*
Ruthrich et al., "Increase of Guanosine Incorporation into RNA of Hippocampal Neurons by Application of Uridine Monophosphate During a Learning Experiments," Brain Research, 69(1), 49-55 (Mar. 29, 1974); only abstract supplied.*
Ott et al. (II), "Influence of 6-Azauridine on Facilitation of Relearning by Precursors of Ribonucleic Acid," Psychopharmacologia, 23(3), 272-278 (1972);Chemical Abstracts, 76(25), p. 103, Abstr. No. 149588z, (Jun. 19, 1972).*
Page et al., "Development Disorder Associated with Increased Cellular Nucleotidase Activity," Proc. National Academy of Science USA, 94(21), 11601-11606 (Oct. 14, 1997).*

(Continued)

Primary Examiner — Lawrence E Crane
(74) Attorney, Agent, or Firm — Pearl Cohen Zedek Latzer, LLP; Mark S. Cohen

(57) ABSTRACT

The present invention provides methods of stimulating or enhancing production of a cellular membrane, improving a cognitive function or a neurological function, treating or ameliorating a decline in a cognitive function or a neurological function, increasing cytidine levels, or treating a neurological disorder in a subject, comprising administering a uridine, a uridine precursor, or a derivative or metabolite thereof to the subject. The invention also provides methods of improving neural function, comprising contacting the neuron with a uridine, a uridine precursor, or a derivative or metabolite thereof.

10 Claims, 25 Drawing Sheets

OTHER PUBLICATIONS

Merlini et al., "Effects of Large Doses of Pyrimidine Nucleosides Cytidine and Uridine in Elderly Patients with Neuropsychological Disturbances Caused by Vascular and Cerebral Metabolic Insufficiency," *Gazzetta Medica Italiana Archivio Scienze Mediche*, 145(6), 379-390 (Jun. 1966); *Biological Abstract*, 83, Abstract No. 27367 (1987).*

Gallai et al. (I), "Effects of Uridien in the Treatment of Diabetic Neuropathy: An Electrophysiologica Study," *Acta Neurol. Scand.*, 86(1), 3-7 (1992); *Biological Abstracts*, 94, Abstract No. 112030 (1992).*

Gallai et al. (II), "Multi-Infarct Dementia: Modification of the P300 Cognitive Event-Related Potential in Patients Treated with the Association of Cytidine and Uridine," *Rivista di Neuropsichiatra e Science Affini*, 41(1), 1-9 (1995); BIOSIS, 1996, Abstract Citation No. 466219; only Abstract supplied.*

Drago et al., "Memory Deficits of Aged Male Rats Can Be Improved by Pyrimidine Nucleosides and N-Acetylglutamine," *Clinical Neuropharamcology*, 13(4), 290-296 (1990); *Biological Abstracts*, 90, Abstract No. 91117 (1990).*

Manna et al., "Effects of Short-Term Adminstration of Cytidine, Uridine and L-Glutmain Alone or in Combination on the Cerebral Electrical Activity of Patients with Chronic Cerebrovascular Disease," *Intl. Journal Clinical Pharmacology Research*, 8(3), 199-210 (1988); *Biological Abstracts*, 86, Abstract No. 51989 (1988).*

Keilbaugh et al., "Anti-Human Immunodeficiencey Virus Type 1 Therapy and Peripheral Neuropathy: Prevention of 2', 3'-Dideoxycytidine Toxicity in PC12 Cells, a Neuronal Model, by Uridine and Pyruvate," *Molecular Pharamcology*,44(4), 702-706 (Oct. 1, 1993); BIOSIS, 1994, Abstract Citation No. 413648.*

Popov et al., "Protective Effect of Uridineof D-Galactosamine-Induced Deficiency in Brain Uridine Phosphates," *Biomedica Biochimica Acta*, 43(12), 1399-1044 (1984); *Biological Abstracts*, 80, Abstract No. 34525 (1985).*

Ingraham et al., "Nucleoside Diphosphokinase from *Salmonella typhimurium*," Chapter 48 in *Methods in Enzymology*, LI(vol. 51), Hoffee et al. (eds.), New York, NY, 1978, Academic Press, only pp. 371 and 375 supplied; assorted portions of other chapters wiere also supplied including pp. 305, 306, 318, 327, 329 and 330.*

Entingh et al., "Brain Uridine Monophosphate: Reduced Incorporation of Uridine During Avoidance Learning," *Brain Research*, 70(1), 131-138 (Apr. 12, 1974); on abstract supplied.*

Rüthrich et al., "Increase of Guanosine Incorporation into RNA of Hippocampal Neurons by Application of Uridine Monophosphate During a Learning Experiments," *Brain Research*, 69(1), 49-55 (Mar. 29, 1974); only abstract supplied.*

Ott et al. (II), "Influence of 6-Azauridine on Facilitation of Relearning by Precursors of Ribonucleic Acid," *Psychopharmacologia*, 23(3), 272-278 (1972); *Chemical Abstracts*, 76(25), p. 103, Abst. No. 149588z, (Jun. 19, 1972).*

Lodish et al., *Molecular Cell Biology*, W. H. Freeman & Co., New York, NY, 2000, only pp. 68-78 supplied, see especiallly pp. 75-76.*

Zaffaroni et al., "Adrenal Conversion of C¹⁴ Labeled Cholesterol and Acetate to Adrenal Cortical Hormones," *Journal of the American Chemical Society*, 73, 1390-1391 (Mar. 1951).*

Gallai et al. (II), "Multi-Infarct Dementia: Modification . . . Patients Treated . . . Cytidine and Uridine," Rivista di Neuropsichiatria e Science Affini, 41(1),.1-9 (1995); BIOSIS, 1996, Abstt Citation No. 466219; only abstract supplied.*

Ruthrich et al., "Increase of Guanosine Incorporation into RNA of . . . Application of Uridine Monophosphate During a Learning Experiments," Brain Research, 69(1), 49-55 (Mar. 29, 1974); only abstract supplied.*

Beers et al. (eds.), a portion of "Nutritional Disorders," Chapter 1 in The Merck Manual of Diagnosis and Therapy, 17th Edition, Merck & Co., Inc., Rahway, NJ, Jan. 1999, only title pages and text pp. 1 ad 12-21 supplied.*

Page et al., "Developmental Disorder Associated with Increased Cellular Nucleotidase Activity," Proc. National Academy of Sciences USA, 94(21), 11601-11606 (Oct. 14, 1997).*

Coirault et al., "Uridine 5-Triphosphate in Therapy. I. Cure of Neurogenic Muscular Atrophy," La Presse Medicale(Fr.), 68(29), 1127-1129 (Jun. 11, 1960); Chemical Abstracts, 57(7), p. 73, Abstract No. 10485f (Oct. 1, 1962).*

Merlini et al., "Effects of . . . Cytidine and Uridine in Elderly Patients with . . . Metabolic Insufficiency," Gazzetta Medica Italiana Archivio Scienze Mediche, 145(6), 379-390 (Jun. 1966); Biological Abtracts, 83, Abstract No. 27367 (1987).*

Gallai et al. (I), "Effects of Uridine in the Treatment of Diabetic Neuropathy: An Electrophysiological Study," Acta Neurol. Scand., 86(1), 3-7 (1992); Biological Abtracts, 94, Abstract No. 112030 (1992).*

Gallai et al. (II), "Multi-Infarct Dementia: Modification . . . Patients Treated . . . Cytidine and Uridine," Rivista di Neuropsichiatria e Science Affini, 41(1), 1-9 (1995); BIOSIS, 1996, Abstt Citation No. 466219; only abstract supplied.*

Drago et al., "Memory Deficits of Aged Male Rats Can Be Improved by Pyrimidine Nucleosides and N-Acetylglutamine," Clinical Neuropharmacology, 13(4), 290-296 (1990); Biological Abstracts, 90, Abstract No. 91117 (1990).*

Manna et al., "Effects of Short-Term Administration of Cytidine, Uridine and L-Glutamine . . . Patients with Chronic Cerebrovascular Disease," Intl. J. Clinical Pharmacology Res., 8(3), 199-210 (1988); Biological Abstracts, 86, Abstract No. 51989 (1988).*

Keilbaugh et al., "Anti-HIV Type 1 Therapy and Peripheral Neuropathy: Prevention of 2', 3'-Dideoxycytidine Toxicity . . . by Uridine and Pyruvate," Molecular Pharmcology, 44(4), 702-706 (Oct. 1, 1993); BIOSIS, 1994, Abstract No. 413648.*

Popov et al., "Protective Effect of Uridine on D-Galactosamine-Induced Deficiency in Brain Uridine Phosphates," Biomedica Biochimica Acta, 43(12), 1399-1404 (1984); Biological Abstracts, 80, Abstract No. 34525 (1985).*

Ingraham et al., "Nucleoside Diphosphokinase from Salmonella . . . ," Chapter 48 et seq. in Methods in Enzymology, LI(vol. 51), Hoffee et al. (eds.), New York, NY, 1978, Academic Press, only pages supplied were 371, 375 305, 306, 318, 327, 329 and 330.*

Miyazaki et al., "Effects of Nucleotides on Learning and Memory in a Morris Water Maze Test in Normal and Basal Forebrain-Lesioned Rats," Life Sciences, 64(1), 45-52 (Nov. 27, 1998).*

Entingh et al., "Brain Uridine Monophosphate: Reduced Incorporation of Uridine During Avoidance Learning," Brain Research, 70(1), 131-138 (Apr. 12, 1974); only abstract supplied.*

Ruthrich et al., "Increase of Guanosine Incorporation into RNA of . . . Application of Uridine Monophosphate During a Learning Experiments," Brain Research, 69(1), 49-55 (Mar. 29, 1974).*

Ott et al. (I), "Effects of RNA Precursors on Development and Maintenance of Long-Term Memory," Psychopharmacologia, 28(2), 195-204 (1973); Chemical Abstracts, 78(19), p. 77, Abstr. No. 119731q, (May 14, 1973).*

Ott et al. (II), "Influence of 6-Azauridine on Facilitation of Relearning by Precursors of Ribonucleic Acid," Psychopharmacologia, 23(3), 272-278 (1972); Chemical Abstracts, 76(25), p. 103, Abstr. No. 149588z, (Jun. 19, 1972).*

A. Lehninger, Biochemistry, Second Edition, Worth Publishers, Inc., New York, NY, Jul. 1978, only pp. 735-737 supplied.*

Gibbons et al., Biochemistry of Cholesterol, Elsevier Biomedical Press, New York , NY, 1982, only pp. 258 and 259 supplied.*

Lodish et al., Molecular Cell Biology, W. H. Freeman & Co., New York, NY, 2000, only pp. 68-78 supplied, see especially pp. 75-76.*

Zaffaroni et al., "Adrenal Conversion of C14 Labeled Cholesterol and Acetate to Adrenal Cortical Hormones," Journal of the American Chemical Society, 73, 1390-1391 (Mar. 1951).*

Kato et al., "Determinants of Sex Hormone Levels in Men as Useful Indices in Hormone-Related Disorders," Journal of Clinical Epidemiology, 45(12), 1417-1421 (Dec. 1992).*

Marcus et al., "Water Soluble Vitamins," Ch. 63 in Goodman & Gilman's The Pharmacological Basis of Therapeutics, 8th Edition, Pergamon Press, Elmsford, NY, 1990, only pp. 1530 and 1542-1544 supplied.*

Sitaram et al., "Human Serial Learning: Enhancement with Arecholine and Choline and Impairment with Scopolamine," Science, 201, 274-276 (Jul. 1978).*

Beers et al. (eds.), a portion of "Nutritional Disorders," Chapter 1 in the Merck Manual of Diagnosis and Therapy, 17th Edition, Merck & Co., Inc., Rahway, NJ, Jan. 1999, only title and text pp. 1 & 12-21 supplied.*
Albright et al., "Choline Availability Alters Embryonic Development of the Hippocampus and Septum in the Rat," Developmental Brain Research, 113, 13-20 (1999).*
Cornford et al, Independent blood-brain barrier transport systems for nucleic acid precursors, Biochim Biophys Acta, 349:211-219, (Jun. 25, 1975).
Dawson, Enzymatic conversion of uridine nucleotide to cytidine nucleotide by rat brain. J Neurochem, 15:31-34, (Jan. 1968).
Becroft DM, et al, Hereditary orotic aciduria: long-term therapy with uridine and a trial of uracil Pediair, 75(5): 885-891, (Oct. 1969).
Roberts CA, et al, Uridine anticonvulsant effects: selective control of nucleoside incorporation in experimental epilepsy. Epilepsia, 15(4): 479-500, (Dec. 1974).
Monticone GF, et al., On the therapeutic use of nucleosides, cytidine and uridine, in some neurological diseases Minerva Med., 57(101): 4348-4352, (Dec. 19, 1966).
Lopez-Coviella et al., Evidence that 5'-cytidinephosphocholine can affect brain phospholipid composition by increasing choline and cytidine plasma levels J Neurochemistry, 65: 889-894, (Aug. 1995).
Ginsburg et al., Rodent models of cerebral ischemia Stroke 20:1627-1642, (Dec. 1989).
Spiers et al, Citicoline improves verbal memory in aging. Arch Neurol, 53(5): 441-448, May 1996.
Hoffee et al, Purine and pyrimidine nucleotide metabolism Methods in Enzymology, vol. LI, pp. 38-48.1978, Academic Press, New York.
Camiener, Studies of the Enymatic deamination of cytosine arabinoside-I, Pharmacology, 14: 1405-1416, 1965.
Cheal, The Gerbil: A Unique Model for Research on Aging, Experimental Aging Res 12(1): 3-11, 1986.
Vincent, et al, The Pathology of the Mongolian Gerbil (*Meriones unguiculatus*): A review Lab Animal Science 29(5): 645-651, Oct. 1979.
Ross et al, Phospholipid Biosynthetic Enzymes in Human Brain, Lipids, 32(4): 351-358, 1997.
De Bruin et al, "Effects of Uridine/Choline on cognitive deficits in spontaneously hypertensive rats" 2002 Society of Neuroscience Meeting, online abstract viewer.
Connolly et al, Uridine and its nucleotides: biological actions, therapeutic potentials. May 1999 20: 218-225.
De Bruin et al, "Effects of Uridine/Choline on cognitive deficits in spontaneously hypertensive rats" Program No. 184.16. 2002 Abstract Viewer/Itinerary Planner. Washington, DC: Society for Neuroscience, 2002. Online: http://sfn.scholarone.com/itin2002/index.html.
Wurtman et al, Effect of oral CDP-choline on plasma choline and uridine levels in humans. Biochem Pharmacol. Oct. 1, 2000;60(7):989-92.
Petersen et al, Mild cognitive impairment clinical characterization and outcome. Arch Neurol. Mar. 1999;56(3):303-8. Erratum in: Arch Neurol Jun. 1999;56(6):760.
Agnati et al, intravenous uridine treatment antagonizes hypoglycaemia-induced reduction in brain somatostatin-like immunoreactivity. Acta Physiol Scand. Apr. 1986;126(4):525-31.
Marcus, et al (1990) "Water soluble vitamins" Ch. 63 in Goodman & Gilman's The Pharmacological Basis of Therapeutics 1530 and 1542-1544.
Sitaram, et al (1978) "Huma Serial Learning: Enhancement with Arecholine and Choline and Impairment with Scopolamine" Science 201, 274-276.
Hock, et al. (2000) "Increased CSF Levels of Nerve Growth Factor in Patients with Alzheimer's Disease" Neurology 54 2009-2011.
Savendahl, et al (1997) "Prolonged Fasting in Humans Results in Diminished Plasma Choline Concentrations But Does Not Cause Liver Dysfuction" American Journal of Clinical Nutrition, 66, 622-625.
Beers, et al (1999) "Ther Merck Manual of Diagnosis and Therapy" 977, 1025, 1027, 1038, 1471, 1472, 1475 and 2417.

Weiss (1995) "Metabolism and Action of CDP-Chlorine as an Endogenous Compound and Administered Exogenously as Citicoline." Life Science vol. 56 No. 9 637-660.
Alveraz, et al (1997) "Citicoline Improves Memory Performance in Elderly Subjects." Methods Find Exp Clin. Pharmacol. 201-210.
Petkov, et al (1993) "Effects of Cytidine Diphosphate Choline on Rats with Memory Deficits." Drug Res. 822-828.
Secades, et al (1995) "CDP-Choline: Pharmalogical and Clinical Review." Methods Find Exp Clin. Pharmacol. 1-54.
D'Orlando et al. "Citicoline (CDP-choline): mechanisms of action and effects in ischemic brain injury." Neurol. Res., vol. 17(4), pp. 281-284. Aug. 1995.
Hull A.M., "Neuroimaging findings in post-traumatic stress disorder." Br. J. Psychiatry. Aug. 2002, vol. 101, pp. 102-110; abstract.
Pawlak R et al. "Tissue plasminogen activator and plasminogen mediate stress-induced decline of neuronal and cognitive functions in the mouse hippocampus." Proc. Natl. Acad. Sci. USA. Dec. 13, 2005, vol. 102, No. 50, pp. 18201-18206; abstract.
Spiers et al "Citicoline Improves Verbal Memory in Aging" Archives of Neuroology, American Medical Association, vol. 43, No. 5, 1996, pp. 441-448.
Fujio et al. Biosci. Biotechnol. Biochem., vol. 61 (6), pp. 956-959. Jun. 1997.
Osada et al. Br. J. Nutr., vol. 62 (2), pp. 343-348. Sep. 1989.
Cacabelos et al "Therapeutic Effects of CDP-Choline in Alzheimer's Disease Cognition, Brain Mapping, Cerebrovascular hemodynamics, and Immune Factors" Annals of the New York Academy of Sciences, New York Academy of Sciences, New York, NY, US, 1996, p. 399-403, ISSN: 0077-8923 abstract.
Albright et al "Choline Availability Alters Embroyonic Development of the Hippocampus and Septum in the Rat", Developmental Brain Research, 11313-20(1999).
Jansen et al "Biosynthesis of Phosphatidylcholine from a Phosphocholine Precurser Pool Derived from the Late Endosomal/Lysosomal Degradation of Sphingomyelin" J.Biological Chemisty, 276(22), 18722-18727 (2001).
O'Neil et al The Merck Index, An Encyclopeida of Chemicals, Drugs, and Biologicals, 13th Edition, 2001, Merck & Co. Whitehouse Station, NJ, p. 404.
Styrer Lubert: "Biochemistry", Third Edition, W.H. Freeman and Company / New York; 1988, p. 550.
Terry R.D. et al.: "Physical basis of cognitive alterations in Alzheimer's disease: synapse loss is the major correlate of cognitive impairment". Ann. Neurol., 1991; 30:572-280.
Berckendridge W.C. et al.: "The lipid composition of adult rat brain synaptosomal plasma membranes", Biochim. Biophys. Acta, 1972, 266:695-707.
Choy P. et al.: "An increase in cytoplasmic CTP accelerates the reaction catalysed by CTP: phosphocholine cytidyltransferase in poliovirus-infected HeLa". The Journal of Biological Chemistry, 1980, 255(3): 1070-1073.
Millington & Wurtman, J. Neurochem 38:1748, 1982.
Ross et al., "Phospholipid biosynthetic enzymes in human brain." Lipids 1997;32:351-8.
Cohen et al., JAMA 274:902, 1995.
Welner et al., American Journal of Public Health, vol. 89, Issue 11 1637-1640 1999.
Schnider-Helmert and Spinweber, Psychopharmacology (Berl). 1986 ;89 (1):1-7.
Judith Wurtman; Sources of Choline and Lecithin in the Diet, Nutrition & The Brain, vol. 5, A. Barbeau, J.H. Growdon, & R.J.Wurtman, eds, Raven Press, New York, 1979, pp. 73-81.
Office Action of the corresponding Chinese patent application No. 200780039887.3 dated Jul. 21, 2010.
Chen T-H et al.: "A nucleoside-nucleotide mixture may reduce memory deterioration in old senescence-accelerated mice." Journal of Nutrition 2000 US, vol. 130, No. 12, 2000, pp. 3085-3089.
Liu L-S et al.: "Uridine prodrug PN401 improves memory in APP2576 mice that model Alzheimer's disease and uridine decreases cell death due to chemical hypoxia in fibroblasts from patients with sporadic AD." Journal of Neurological Sciences; 3rd International Congress on Vascular Dementia; Prague, Czech Republic; Oct.

23-26, 2003, Elsevier Scientific Publishing Co, Amsterdam, NL, vol. 229, no. Special Issue SI, Mar. 1, 2005, pp. 316-317.

Villardita C et al.: "Effects of pyrimidine nucleosides and N-acetyl-glutamine on learning and memory processes in men of various ages." ACTA Therapeutica, XX, XX, vol. 9, No. 4, Jan. 1, 1983, pp. 407-416.

De Bruin N M W J et al.: "Combined uridine and choline administration improvies cognitive deficits in spontaneously hypertensive rats." Neurobiology of Learning and Memory 200307 US LNKD-DOI:10.1016/S1074-7427(03)00024-8, vol. 80, No. 1, Jul. 2003, pp. 63-79.

Extended European Search Report and Search Opinion for corresponding EP application No. 07717110.6, dated Oct. 14, 2010.

Teather L-A et al.: "Chronic administration of UMP ameliorates the impairment of hippocampal-dependent memory in impoverished rats." Journal of Nutrition, vol. 136, No. 11, Nov. 2006. pp. 2834-2837.

International Preliminary Report on Patentability for corresponding PCT application No. PCT/US05/32312, dated Oct. 4, 2010.

Cacabelos R. et al, "Therapeutic effects of CDP-Choline in Alzheimer's disease cognition, brain mapping, cerebrovascular hemodynamics, and immune factors." Annals New York Academy of Sciences, 777:399-403, (Dec . 17, 2006).

Franco-Maside A. et al: "Brain Mapping Activity and Mental Performance After Chronic Treatment with CDP-Choline in Alzheimer's Disease," Methods and Findings in Experimental and Clinical Pharmacology, Prous, Barcelona, ES, vol. 16, No. 8, Jan. 1, 1994, pp. 597-607.

Supplementary European Search Report of corresponding European Application No. 07 83 7399, dated Nov. 26, 2010.

Supplementary European Search Report of corresponding European Application No. 05796529, dated Jan. 20, 2011.

Extended European Search Report of corresponding EP Application No. 10075660 dated Jun. 20, 2011.

Extended European Search Report of corresponding EP Application No. 10075661 dated Jun. 20, 2011.

Piccoli F et al., "CDP-choline in the treatment of chronic cerebrovasculopathies," Archives of Gerontology and Geriatrics, vol. 18, No. 3, 1994, pp. 161-168.

Karkishchenko N N et al., "Use of uridine as antidepressant—shows its reduced toxicity and elimination of several harmful side effects," Derwent, 1993, abstract.

Petkov V.D. et al., "Effect of CDP-Choline on Learning and Memory Processes in Rodents," Meth Find Exp Clin Pharmacol, 1992. 14(8), pp. 593-605.

Barker et al., "Age-Associated Memory Impairment: Diagnostic and Treatment Issues," International Journal of Geriatric Psychiatry, 8(4), 305-310 (Apr. 1993).

Geiger et al., "Cytidine and Uridine Requirement of the Brain," Journal of Neurochemistry, 1, 93-100 (1956).

* cited by examiner

A

B

Increased Ach basal concentration with UMP treatment
N=6 rats each group for control, 0.1%, 0.5% and 2.5% UMP.
Data represented Mean+/-SEM. One-way ANOVA followed
by Turky post hoc tests were used for multiple comparisons.
The significance level was set at p<0.05.

A.

B.

A.

Length of NGF Treatment (days)

B.

URIDINE ADMINISTRATION STIMULATES MEMBRANE PRODUCTION

CROSS REFERENCE TO RELATED APPLICATIONS

This application is a Continuation-in-Part of U.S. application Ser. No. 10/941,025, filed Sep. 15, 2004, which is a Continuation-in-Part of U.S. application Ser. No. 09/363,748, filed Jul. 30, 1999, now U.S. Pat. No. 6,989,376, which claims priority from U.S. Provisional Patent Application 60/095,002, filed Jul. 31, 1998, now expired, all which are incorporated herein by reference in their entirety.

STATEMENT REGARDING FEDERALLY SPONSORED RESEARCH OR DEVELOPMENT

The invention described herein was supported in part by grants from The National Institutes of Mental Health (Grant No. 2 R01 MH-28783-28) and The Center for Brain Sciences and Metabolism Charitable Trust.

FIELD OF THE INVENTION

The present invention provides methods of stimulating or enhancing production of a cellular membrane, improving a cognitive function or a neurological function, treating or ameliorating a decline in a cognitive function or a neurological function, increasing cytidine levels, or treating a neurological disorder in a subject, comprising administering a uridine, a uridine precursor, or a derivative or metabolite thereof to the subject. The invention also provides methods of improving neural function, comprising contacting the neuron with a uridine, a uridine precursor, or a derivative or metabolite thereof.

BACKGROUND OF THE INVENTION

Uridine is a pyrimidine nucleoside and is essential in the synthesis of ribonucleic acids and tissue glycogens such as UDP glucose and UTP glucose. Prior medical uses of uridine alone include treatment of genetic disorders related to deficiencies of pyrimidine synthesis such as orotic aciduria.

SUMMARY OF THE INVENTION

In one embodiment, the present invention provides a method of stimulating or enhancing production of a membrane of a brain cell of a subject, comprising administering to the subject a uridine, whereby the uridine stimulates a P2Y receptor in the brain cell, thereby stimulating or enhancing production of a membrane of a brain cell of a subject. In another embodiment, the present invention provides a method of stimulating or enhancing production of a membrane of a brain cell of a subject, comprising administering to the subject a uridine derivative, whereby the uridine derivative stimulates a P2Y receptor in the brain cell, thereby stimulating or enhancing production of a membrane of a brain cell of a subject. In another embodiment, the present invention provides a method of stimulating or enhancing production of a membrane of a brain cell of a subject, comprising administering to the subject a uridine metabolite, whereby the uridine metabolite stimulates a P2Y receptor in the brain cell, thereby stimulating or enhancing production of a membrane of a brain cell of a subject.

In another embodiment, the brain cell of the present invention is newly differentiated. In another embodiment, the brain cell is not newly differentiated. Each possibility represents a separate embodiment of the present invention.

In another embodiment, the present invention provides a method of stimulating or enhancing production of a membrane of a neural cell of a subject, comprising administering to the subject a uridine, whereby the uridine stimulates a P2Y receptor in the neural cell, thereby stimulating or enhancing production of a membrane of a neural cell of a subject. In another embodiment, the present invention provides a method of stimulating or enhancing production of a membrane of a neural cell of a subject, comprising administering to the subject a uridine derivative, whereby the uridine derivative stimulates a P2Y receptor in the neural cell. In another embodiment, the present invention provides a method of stimulating or enhancing production of a membrane of a neural cell of a subject, comprising administering to the subject a uridine metabolite, whereby the uridine metabolite stimulates a P2Y receptor in the neural cell.

In another embodiment, the present invention provides a method of stimulating or enhancing production of a membrane of a brain cell of a subject, comprising administering to the subject a uridine, whereby the uridine is converted to a second compound that stimulates a P2Y receptor in the brain cell, thereby stimulating or enhancing production of a membrane of a brain cell of a subject. In another embodiment, the present invention provides a method of stimulating or enhancing production of a membrane of a brain cell of a subject, comprising administering to the subject a uridine derivative, whereby the uridine derivative is converted to a second compound that stimulates a P2Y receptor in the brain cell. In another embodiment, the present invention provides a method of stimulating or enhancing production of a membrane of a brain cell of a subject, comprising administering to the subject a uridine metabolite, whereby the uridine metabolite is converted to a second compound that stimulates a P2Y receptor in the brain cell.

In another embodiment, the present invention provides a method of stimulating or enhancing production of a membrane of a neural cell of a subject, comprising administering to the subject a uridine, whereby the uridine is converted to a second compound that stimulates a P2Y receptor in the neural cell, thereby stimulating or enhancing production of a membrane of a neural cell of a subject. In another embodiment, the present invention provides a method of stimulating or enhancing production of a membrane of a neural cell of a subject, comprising administering to the subject a uridine derivative, whereby the uridine derivative is converted to a second compound that stimulates a P2Y receptor in the neural cell. In another embodiment, the present invention provides a method of stimulating or enhancing production of a membrane of a neural cell of a subject, comprising administering to the subject a uridine metabolite, whereby the uridine metabolite is converted to a second compound that stimulates a P2Y receptor in the neural cell.

In another embodiment, the present invention provides a method of stimulating or enhancing production of a membrane of a brain cell, comprising contacting the brain cell with a uridine, whereby the uridine stimulates a P2Y receptor in the brain cell, thereby stimulating or enhancing production of a membrane of a brain cell. In another embodiment, the present invention provides a method of stimulating or enhancing production of a membrane of a brain cell, comprising contacting the brain cell with a uridine derivative, whereby the uridine derivative stimulates a P2Y receptor in the brain cell, thereby stimulating or enhancing production of a membrane of a brain cell. In another embodiment, the present invention provides a method of stimulating or enhancing production of a membrane of a brain cell, comprising contacting the brain cell with a uridine metabolite, whereby the uridine metabolite stimulates a P2Y receptor in the brain cell, thereby stimulating or enhancing production of a membrane of a brain cell.

In another embodiment, the present invention provides a method of stimulating or enhancing production of a membrane of a neural cell, comprising contacting the neural cell with a uridine, whereby the uridine stimulates a P2Y receptor in the neural cell, thereby stimulating or enhancing production of a membrane of a neural cell. In another embodiment, the present invention provides a method of stimulating or enhancing production of a membrane of a neural cell, comprising contacting the neural cell with a uridine derivative, whereby the uridine derivative stimulates a P2Y receptor in the neural cell. In another embodiment, the present invention provides a method of stimulating or enhancing production of a membrane of a neural cell, comprising contacting the neural cell with a uridine metabolite, whereby the uridine metabolite stimulates a P2Y receptor in the neural cell.

In another embodiment, the present invention provides a method of stimulating or enhancing production of a membrane of a brain cell, comprising contacting the brain cell with a uridine, whereby the uridine is converted to a second compound that stimulates a P2Y receptor in the brain cell, thereby stimulating or enhancing production of a membrane of a brain cell. In another embodiment, the present invention provides a method of stimulating or enhancing production of a membrane of a brain cell, comprising contacting the brain cell with a uridine derivative, whereby the uridine derivative is converted to a second compound that stimulates a P2Y receptor in the brain cell. In another embodiment, the present invention provides a method of stimulating or enhancing production of a membrane of a brain cell, comprising contacting the brain cell with a uridine metabolite, whereby the uridine metabolite is converted to a second compound that stimulates a P2Y receptor in the brain cell.

In another embodiment, the present invention provides a method of stimulating or enhancing production of a membrane of a neural cell, comprising contacting the neural cell with a uridine, whereby the uridine is converted to a second compound that stimulates a P2Y receptor in the neural cell, thereby stimulating or enhancing production of a membrane of a neural cell. In another embodiment, the present invention provides a method of stimulating or enhancing production of a membrane of a neural cell, comprising contacting the neural cell with a uridine derivative, whereby the uridine derivative is converted to a second compound that stimulates a P2Y receptor in the neural cell. In another embodiment, the present invention provides a method of stimulating or enhancing production of a membrane of a neural cell, comprising contacting the neural cell with a uridine metabolite, whereby the uridine metabolite is converted to a second compound that stimulates a P2Y receptor in the neural cell.

In another embodiment, the present invention provides a method of improving a cognitive function in a subject, comprising administering a uridine, a derivative or metabolite thereof, or a precursor thereof to the subject, thereby improving a cognitive function in a subject.

In another embodiment, the present invention provides a method of treating or ameliorating a decline in a cognitive function in a subject, comprising administering a uridine, a derivative or metabolite thereof, or a precursor thereof to the subject, thereby inhibiting or preventing a decline in a cognitive function in a subject.

In another embodiment, the present invention provides a method of improving or enhancing a neurological function in a subject, comprising administering a uridine, a derivative or metabolite thereof, or a precursor thereof to the subject, thereby improving or enhancing a neurological function in a subject.

In another embodiment, the present invention provides a method of increasing a level of cytidine, cytidine triphosphate, CDP-choline, or a derivative or metabolite thereof in a tissue or plasma of a subject, comprising administering a uridine, a derivative or metabolite thereof, or a precursor thereof to the subject, thereby increasing a level of cytidine, cytidine triphosphate, CDP-choline, or a derivative or metabolite thereof in a tissue or plasma of a subject.

In another embodiment, the present invention provides a method of stimulating or enhancing an amount of or a synthesis of a membrane of a cell, comprising contacting the cell with a uridine or a derivative or metabolite thereof, thereby stimulating or enhancing an amount of or a synthesis of a membrane of a cell.

In another embodiment, the present invention provides a method of stimulating or enhancing an outgrowth of a neurite of a neural cell, comprising contacting the neural cell with a uridine or a derivative or metabolite thereof, thereby stimulating or enhancing an outgrowth of a neurite of a neural cell.

In another embodiment, the present invention provides a method of increasing a number of neurites of a neural cell, comprising contacting the neural cell with a uridine or a derivative or metabolite thereof, thereby increasing a number of neurites of a neural cell.

In another embodiment, the present invention provides a method of stimulating or enhancing a branching of a neurite of a neural cell, comprising contacting the neural cell with a uridine or a derivative or metabolite thereof, thereby stimulating or enhancing a branching of a neurite of a neural cell.

In another embodiment, the present invention provides a method of increasing a level of a neurotransmitter in a synapse, comprising contacting a neural cell adjacent to the synapse with a uridine or a derivative or metabolite thereof, thereby increasing a level of the neurotransmitter in a synapse.

In another embodiment, the present invention provides a method of increasing a release of a neurotransmitter into a synapse, comprising contacting a neural cell adjacent to the synapse with a uridine or a derivative or metabolite thereof, thereby increasing a release of the neurotransmitter into a synapse.

In another embodiment, the present invention provides a method of increasing a sensitivity of a neuron to a stimulus, comprising contacting the neuron with a uridine or a derivative or metabolite thereof, thereby increasing a sensitivity of a neuron to a stimulus.

DETAILED DESCRIPTION OF THE INVENTION

The present invention is directed to methods of improving cognitive and neurological functions by means of administration of uridine, and is based on the unexpected finding that administration of uridine raises cytidine levels in the brain and in other tissues. Additionally, it was unexpectedly found that uridine stimulates membrane synthesis, neurite outgrowth, and neurotransmitter release in neural cells, providing further evidence that uridine is effective in improving cognitive and neurological functions. Finally, it was shown directly that uridine improves cognitive function in several relevant scientific models of age-related decline in cognitive function, as will be elucidated below.

In one embodiment, the present invention provides a method of improving a cognitive function in a subject, comprising administering a uridine, a derivative or metabolite thereof, or a precursor thereof to the subject, thereby improving a cognitive function in a subject.

In another embodiment, the present invention provides a method of treating or ameliorating a decline in a cognitive function in a subject, comprising administering a uridine, a derivative or metabolite thereof, or a precursor thereof to the subject, thereby inhibiting or preventing a decline in a cognitive function in a subject.

In one embodiment, the cognitive function is memory. The memory is, in one embodiment, spatial memory. In another embodiment, the memory is working memory. In another embodiment, the memory is reference memory. In another embodiment, the memory is short-term memory. In another embodiment, the memory is long-term memory. In another embodiment, the memory is medium-term memory. In another embodiment, the memory is any other type of memory known in the art. Each type of memory represents a separate embodiment of the present invention.

Figure 21:
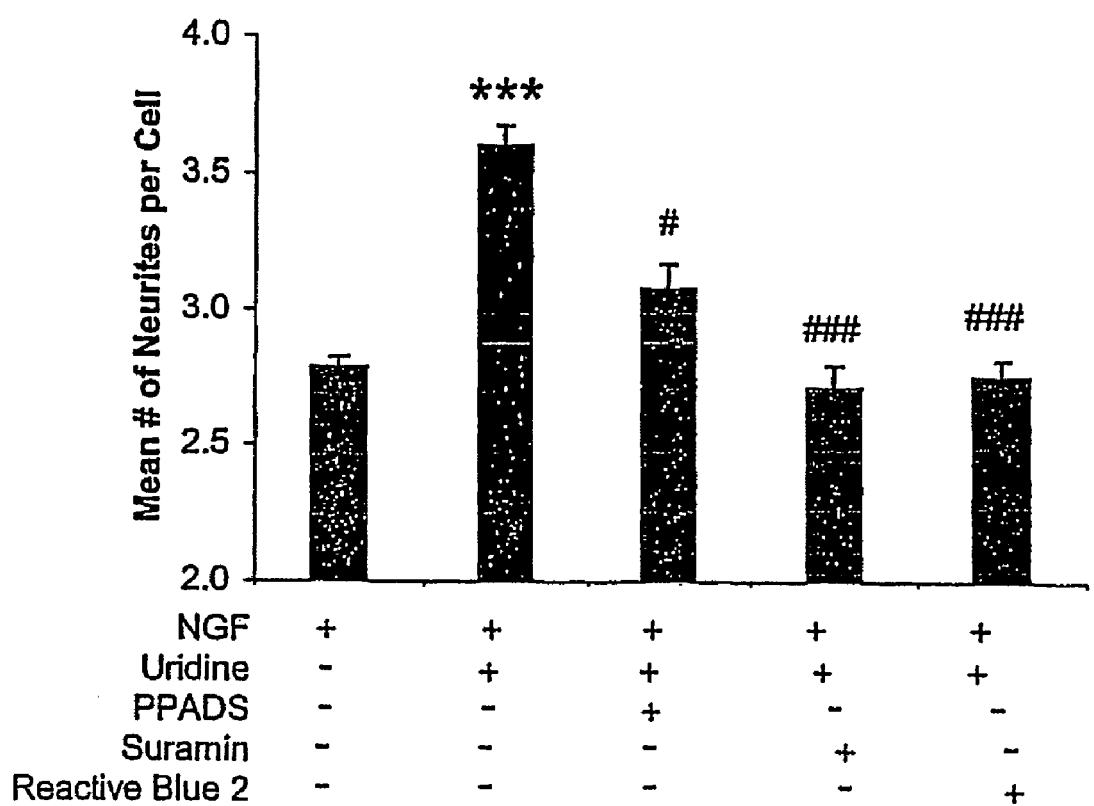
FIG. 21. P2Y receptor antagonists inhibited the effect of uridine on neurite outgrowth. Cells were treated for 4 days with NGF and with or without uridine (100 μM) and the P2Y receptor antagonists PPADS, suramin, or RB-2. Values represent means+SEM. ***$p<0.001$ vs. NGF treatment; #$p<0.05$, ###$p<0.001$ vs. NGF plus uridine treatment.
Figure 22:
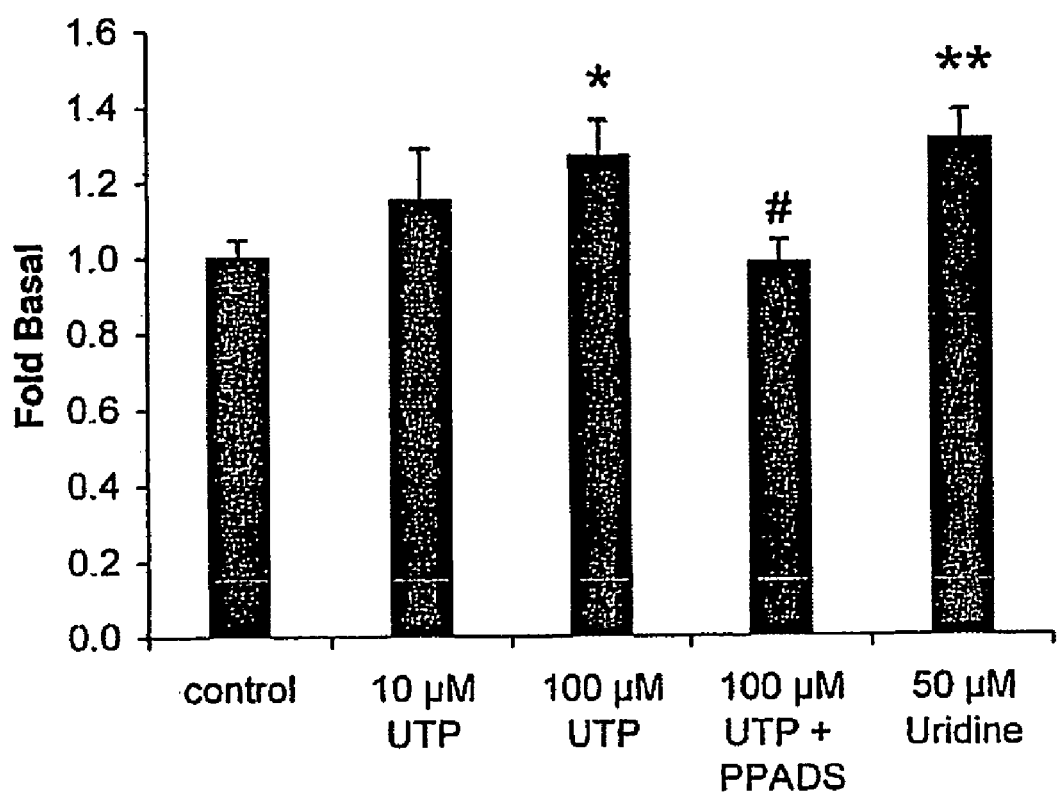
FIG. 22. Phosphatidylinositol (PI) turnover is stimulated by UTP and uridine. Cells were metabolically labeled with [$^3$H]inositol overnight, stimulated with UTP, uridine, or UTP plus PPADS in the presence of lithium at the indicated concentrations, and radio-labeled inositol phosphates derived from PI breakdown were measured by scintillation counting. Values represent means+SEM. *$p<0.05$, **$p<0.01$ vs. control; #$p<0.05$ vs. 100 μM UTP treatment.
Figure 23:
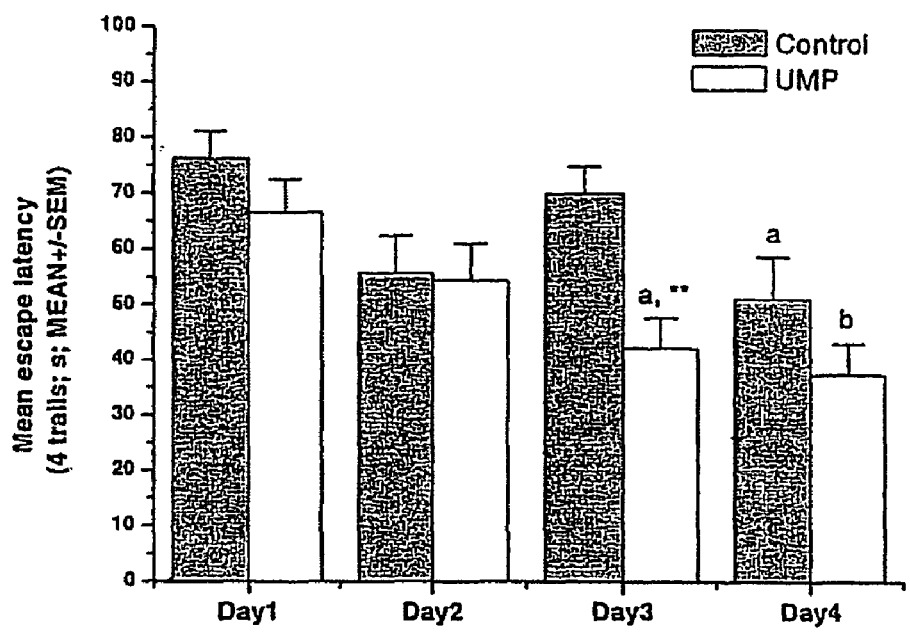
FIG. 23. Oral UMP improves learning and spatial memory in rats. 18-month old rats in restricted environments consumed a control diet or a UMP diet for 6 weeks, and then were tested, using a Morris Water Maze, 4 trials/day for 4 days. Mean time to locate the platform is given in seconds.

For example, the data in FIGS. 21-23 show directly that uridine improves several types of memory. The consistency of the effect across different species in different types of assessments of memory verify the findings of the present invention.

In another embodiment, the cognitive function is learning. The learning is, in one embodiment, cognitive learning. In another embodiment, the learning is affective learning. In another embodiment, the learning is psychomotor learning. In another embodiment, the learning is any other type of learning known in the art. Each type of learning represents a separate embodiment of the present invention.

In another embodiment, the cognitive function is intelligence. In one embodiment, the intelligence is linguistic intelligence. In another embodiment, the intelligence is musical intelligence. In another embodiment, the intelligence is spatial intelligence. In another embodiment, the intelligence is bodily intelligence. In another embodiment, the intelligence is interpersonal intelligence. In another embodiment, the intelligence is intrapersonal intelligence. In another embodiment, the intelligence is interpersonal intelligence. In another embodiment, the intelligence is intrapersonal intelligence. In another embodiment, the intelligence is logico-mathematical intelligence. In another embodiment, the intelligence is any other type of intelligence known in the art. Each type of intelligence represents a separate embodiment of the present invention.

In another embodiment, the cognitive function is mental fitness. In another embodiment, the cognitive function is any other type of cognitive function known in the art. Each type of cognitive function represents a separate embodiment of the present invention.

In one embodiment, "improving" a cognitive function, or "improvement" of a cognitive function refer to increasing the capacity of the subject to perform the cognitive function. In another embodiment, the terms refer to an increased or improved baseline level of the cognitive function in the subject. In another embodiment, the terms refer to an increased or improved level of the cognitive function in response to a challenge or test.

In another embodiment, improving a cognitive function refers to effecting a 10% improvement thereof In another embodiment, improving a cognitive function refers to effecting a 20% improvement thereof In another embodiment, improving a cognitive function refers to effecting a 30% improvement thereof. In another embodiment, improving a cognitive function refers to effecting a 40% improvement thereof. In another embodiment, improving a cognitive function refers to effecting a 50% improvement thereof. In another embodiment, improving a cognitive function refers to effecting a 60% improvement thereof. In another embodiment, improving a cognitive function refers to effecting a 70% improvement thereof. In another embodiment, improving a cognitive function refers to effecting an 80% improvement thereof. In another embodiment, improving a cognitive function refers to effecting a 90% improvement thereof. In another embodiment, improving a cognitive ftmction refers to effecting a 100% improvement thereof.

In another embodiment, improvement of a cognitive function is assessed relative to the cognitive function before beginning treatment. In another embodiment, improvement of a cognitive function is assessed relative to an untreated subject. In another embodiment, improvement of a cognitive function is assessed according to a standardized criterion such as, for example, a test or the like. Each type of improvement of cognitive activity represents a separate embodiment of the present invention.

In another embodiment, improvement of a cognitive function is assessed by the number of connections between neurons in the subject's brain. In another embodiment, improvement of a cognitive function is assessed by the number of capillaries in the subject's brain, or in a specific region of the subject's brain. In another embodiment, improvement of a cognitive function is assessed by neural activity. In another embodiment, improvement of a cognitive function is assessed by neural function. In another embodiment, improvement of a cognitive function is assessed by linguistic function. In another embodiment, improvement of a cognitive function is assessed by ability to communicate. In another embodiment, improvement of a cognitive function is assessed by measurement of levels of acetylcholine or other neurotransmitters or brain chemicals correlated with cognitive function. In another embodiment, improvement of a cognitive function is assessed by Positron Emission Tomography (PET) scanning of the subject's brain. In another embodiment, improvement of a cognitive function is assessed by magnetic resonance imaging (MRI) scanning of the subject's brain. In another embodiment, improvement of a cognitive function is assessed by Cognitive Abilities Screening Instrument (CASI) (Peila R et al, Stroke. 32: 2882-9, 2001). In another embodiment, improvement of a cognitive function is assessed by a test such as, for example, the tests disclosed herein (Example 13) Methods for assessing improvement of cognitive function are well known in the art, and are described, for example in Antonova E et al (Schizophr Res. Oct. 1, 2004; 70(2-3):117-45) and in Cognitive Function Analysis (Greenwood Pub Group, 1998). Each such method represents a separate embodiment of the present invention.

"Treating or ameliorating a decline in a cognitive function" refers, in one embodiment, to mitigating the decline. In another embodiment, the phrase refers to preventing the decline. In another embodiment, the phrase refers to reversing the decline. In another embodiment, the phrase refers to slowing the decline. In another embodiment, the phrase refers to halting the decline. Each possibility represents a separate embodiment of the present invention.

In another embodiment, the decline in a cognitive function results from a neurological disorder. In one embodiment, the neurological disorder is a memory disorder. The memory disorder comprises, in one embodiment, a memory decline. In another embodiment, the memory decline is associated with brain aging. In another embodiment, the memory disorder is selected from the group consisting of Pick's disease, Lewy Body disease, and a dementia. In one embodiment, the dementia is associated with Huntington's disease. In another embodiment, the dementia is associated with AIDS dementia. Each possibility represents a separate embodiment of the present invention.

In one embodiment, the neurological disorder is associated with a dopaminergic pathway. In another embodiment, the neurological disorder is not associated with a dopaminergic pathway. Each possibility represents a separate embodiment of the present invention.

In another embodiment, the neurological disorder is a cognitive dysfunction. In one embodiment, the cognitive dysfunction is a dyslexia. In one embodiment, the cognitive dysfunction comprises a lack of attention. In one embodiment, the cognitive dysfunction comprises a lack of alertness. In one embodiment, the cognitive dysfunction comprises a lack of concentration. In one embodiment, the cognitive dysfunction comprises a lack of focus. In one embodiment, the cognitive dysfunction comprises a stroke. In one embodiment, the cognitive dysfunction comprises a multi-infarct dementia. In one embodiment, the cognitive dysfunction comprises minimal cognitive impairment. In one embodiment, the cognitive dysfunction comprises age-related memory impairment. Each possibility represents a separate embodiment of the present invention.

In another embodiment, the neurological disorder is an emotional disorder. In one embodiment, the emotional disorder comprises mania. In another embodiment, the emotional disorder comprises depression. In another embodiment, the emotional disorder comprises stress. In another embodiment, the emotional disorder comprises panic. In another embodiment, the emotional disorder comprises anxiety. In another embodiment, the emotional disorder comprises dysthymia. In another embodiment, the emotional disorder comprises psychosis. In another embodiment, the emotional disorder comprises anxiety. In another embodiment, the emotional disorder comprises a seasonal effective disorder. In another embodiment, the emotional disorder comprises a bipolar disorder.

In another embodiment, the neurological disorder is a depression. In one embodiment, the depression is an endogenous depression. In another embodiment, the depression is a major depressive disorder. In another embodiment, the depression is depression with anxiety. In another embodiment, the depression is bipolar depression. Each type of depression represents a separate embodiment of the present invention.

In another embodiment, the neurological disorder is selected from the group consisting of ataxia and Friedreich's ataxia. In another embodiment, the neurological disorder of the present invention excludes epilepsy, seizures, convulsions, and the like.

In another embodiment, the neurological disorder is a movement disorder. The movement disorder comprises, in one embodiment, a tardive dyskinesia. In another embodiment, the movement disorder comprises a dystonia. In another embodiment, the movement disorder comprises a Tourette's syndrome. In another embodiment, the movement disorder is any other movement disorder known in the art.

In another embodiment, the neurological disorder is a cerebro-vascular disease. The cerebro-vascular disease results, in one embodiment, from hypoxia. In another embodiment, the cerebro-vascular disease results from any other cause capable of causing a cerebro-vascular disease. In another embodiment, the cerebro-vascular disease is cerebral thrombosis. In another embodiment, the cerebro-vascular disease is ischemia.

In another embodiment, the neurological disorder is a behavioral syndrome. In another embodiment, the neurological disorder is a neurological syndrome. In one embodiment, the behavioral syndrome or neurological syndrome follows brain trauma. In another embodiment, the behavioral syndrome or neurological syndrome follows spinal cord injury.

In another embodiment, the behavioral syndrome or neurological syndrome follows anoxia.

In another embodiment, the neurological disorder is a peripheral nervous system disorder. In one embodiment, the peripheral nervous system disorder is a neuromuscular disorder. In another embodiment, the peripheral nervous system disorder is any other peripheral nervous system disorder known in the art. In another embodiment, the neuromuscular disorder is myasthenia gravis. In another embodiment, the neuromuscular disorder is post-polio syndrome. In another embodiment, the neuromuscular disorder is a muscular dystrophy.

Each type of neurological disorder described herein or known in the art represents a separate embodiment of the present invention.

In one embodiment, the uridine precursor that is administered in the present invention is, for example, a uridine-5'-monophosphate (UMP). In another embodiment, the uridine precursor that is administered is a uridine-5'-diphosphate (JDP). In another embodiment, the uridine precursor that is administered is a uridine-5'-triphosphate (UTP). In another embodiment, the uridine precursor that is administered is a cytidine-5'-monophosphate. In another embodiment, the uridine precursor that is administered is UDP glucose. In another embodiment, the uridine precursor that is administered is a cytidine-5'-diphosphate (CDP). In another embodiment, the uridine precursor that is administered is a CDP-glucose. In another embodiment, the uridine precursor that is administered is In another embodiment, any pharmacologically acceptable uridine precursor, derivative or metabolite is utilized. In another embodiment, the composition that is administered comprise the uridine or precursor, derivative or metabolite thereof as the sole active ingredient. Each type of uridine precursor, derivative, or metabolite represents a separate embodiment of the present invention.

In one embodiment, various other uridine-based compounds other than uridine itself serve as uridine sources or uridine precursors. These are uridine-rich food or dietary products like algae; salts of uridine like uridine phosphates, acylated uridine or the like. In another embodiment, therapeutically or pharmacologically effective doses of acyl derivatives of uridine or mixtures thereof, e.g. those disclosed in U.S. Pat. No. 5,470,838 are also administered. Each precursor of uridine represents a separate embodiment of the present invention.

In one embodiment, administration of the uridine, derivative or metabolite thereof, or precursor thereof increases a level of cytidine, cytidine triphosphate, CDP-choline, phosphatidylethanolamine (PE), phosphatidylserine (PS) or a derivative or metabolite thereof in said subject, thereby improving the cognitive function. In another embodiment, the cognitive function is improves without increasing a level of cytidine, cytidine triphosphate, CDP-choline, PE, PS, or a derivative or metabolite thereof Each possibility represents a separate embodiment of the present invention.

In another embodiment, a salt comprising the uridine precursor, derivative or metabolite is utilized in a method of the present invention. In one embodiment, the salt is UMP disodium (Examples 2-3). In another embodiment, the salt is any other pharmacologically acceptable salt of a uridine precursor, derivative or metabolite. In another embodiment, the composition that is administered comprises the salt of the uridine or precursor, derivative or metabolite thereof as the sole active ingredient. Each uridine salt represents a separate embodiment of the present invention.

The term "derivative" in one embodiment refers to a compound chemically related to uridine in such a way that uridine is converted to the derivative in a subject's body. In another embodiment, "derivative" refers to a compound chemically related to uridine in such a way that the derivative is converted to uridine in a subject's body. In one embodiment, the conversion occurs via one or more stable intermediates. In another embodiment, the conversion occurs directly. Each possibility represents a separate embodiment of the present invention.

In one embodiment, the terms "administering" or "administration" refer to bringing a subject in contact with a compound of the present invention. In another embodiment, administration comprises, for example, swallowing the uridine precursor, derivative, or metabolite. In another embodiment, administration comprises imbibing the uridine precursor, derivative, or metabolite. In another embodiment, administration comprises a pharmaceutical composition or the like. In another embodiment, administration comprises a nutritional supplement or the like.

In one embodiment, administration is performed by the subject. In another embodiment, administration is performed by a care provider. In another embodiment, administration is performed by a third party. Each type of administration represents a separate embodiment of the present invention.

In one embodiment, the uridine, derivative, metabolite, or precursor thereof is administered in a dosage of between about 20 milligrams and 50 grams per day. In another embodiment, the uridine, derivative, metabolite, or precursor thereof is administered in a dosage of between about 50 milligrams and 30 grams per day. In another embodiment, the uridine, derivative, metabolite, or precursor thereof is administered in a dosage of between about 75 milligrams and 20 grams per day. In another embodiment, the uridine, derivative, metabolite, or precursor thereof is administered in a dosage of between about 100 milligrams and 20 grams per day. In another embodiment, the uridine, derivative, metabolite, or precursor thereof is administered in a dosage of between about 100 milligrams and 10 grams per day. In another embodiment, the uridine, derivative, metabolite, or precursor thereof is administered in a dosage of between about 200 milligrams and 8 grams per day. In another embodiment, the uridine, derivative, metabolite, or precursor thereof is administered in a dosage of between about 400 milligrams and 6 grams per day. In another embodiment, the uridine, derivative, metabolite, or precursor thereof is administered in a dosage of between about 600 milligrams and 4 grams per day. In another embodiment, the uridine, derivative, metabolite, or precursor thereof is administered in a dosage of between about 800 milligrams and 3 grams per day. In another embodiment, the uridine, derivative, metabolite, or precursor thereof is administered in a dosage of between about 1 and 2.5 grams per day. In another embodiment, the uridine, derivative, metabolite, or precursor thereof is administered in a dosage of between about 1.5 and 2 grams per day. In another embodiment, the uridine, derivative, metabolite, or precursor thereof is administered in a dosage of between about 5 milligrams and 5 grams per day. In another embodiment, the uridine, derivative, metabolite, or precursor thereof is administered in a dosage of between about 5 milligrams and 50 grams per day. Each dosage range represents a separate embodiment of the present invention.

In another embodiment, an additional therapeutic compound is administered to the subject as part of the method of the present invention. In one embodiment, the additional therapeutic compound is a drug that acts as a uridine phosphorylase inhibitor; e.g. benzyl barbiturate or derivatives thereof. In another embodiment, the additional therapeutic compound is a drug that increases uridine availability. In another embodiment, the additional therapeutic compound is a uridine secretion-inhibiting compound, e.g. dilazep or hexobendine. In another embodiment, the additional therapeutic compound is a uridine renal transport competitors, e.g. L-uridine, L-2',3'-dideoxyuridine, and D-2',3'-dideoxyuridine. In another embodiment, the additional therapeutic compound is a drug which acts in synergy with uridine in generation of a phospholipid. In another embodiment, the additional therapeutic compound is a compound which competes with uridine in kidney clearance, e.g. L-uridine, L-2',3'-dideoxyuridine, and D-2',3'-dideoxyuridine or mixtures thereof as disclosed in U.S. Pat. Nos. 5,723,449 and 5,567,689. In another embodiment, the additional therapeutic compound is any other compound that is beneficial to a subject.

In another embodiment, the additional therapeutic compound is a choline-based compound, e.g. choline, choline salts or esters, e.g. choline bitartrate, choline stearate, choline chloride or the like, or compounds that dissociate to choline, such as sphingomyelin, cytidine-diphospho-choline or citicoline or CDP-choline, acylglycerophosphocholines, e.g., lecithin, lysolecithin, glycerophosphatidylcholine, and mixtures thereof. Such compounds, in one embodiment, act in synergy with uridine or uridine precursor. In one embodiment, the choline or compound that dissociates into choline is administered so that a choline level of at least about 20-30 nanomoles in the subject's blood or brain. In another embodiment, a choline level of between 10 and 50 nanomoles is attained in the subject's blood or brain. In another embodiment, a choline level of between 5 and 75 nanomoles is attained in the subject's blood or brain. In another embodiment, a choline level of between 25 and 40 nanomoles is attained in the subject's blood or brain. In another embodiment, a choline level of between 30 and 35 nanomoles is attained in the subject's blood or brain. Each possibility represents a separate embodiment of the present invention.

In another embodiment, the additional therapeutic compound is sphingomyelin, an acylglycerophosphocholine, a lecithin, a lysolecithin, a glycerophosphatidylcholine, and a fatty acid, or a mixture thereof. Each additional therapeutic compound represents a separate embodiment of the present invention.

In another embodiment, improving the cognitive function in the subject is accomplished by increasing a level of cytidine in the subject as a result of administration of the uridine, derivative or metabolite thereof, or precursor thereof. In another embodiment, improving the cognitive function in a subject is accomplished by increasing a level of cytidine triphosphate in the subject. In another embodiment, improving the cognitive function in a subject is accomplished by increasing a level of CDP-choline in the subject. In another embodiment, improving the cognitive function in a subject is accomplished by increasing a level of a derivative of cytidine, cytidine triphosphates, or CDP-choline in the subject. In another embodiment, improving the cognitive function in a subject is accomplished by increasing a level of a metabolite of cytidine, cytidine triphosphates, or CDP-choline in the subject. In another embodiment, increasing the level of cytidine, cytidine triphosphates, CDP-choline, or a derivative or metabolite thereof is partially responsible for mediating improving the cognitive function in the subject. In another embodiment, the uridine, derivative or metabolite thereof, or precursor thereof improves cognitive function without increasing the level of cytidine, cytidine triphosphates, CDP-choline, or a derivative or metabolite thereof. Each possibility represents a separate embodiment of the present invention.

Figure 8:
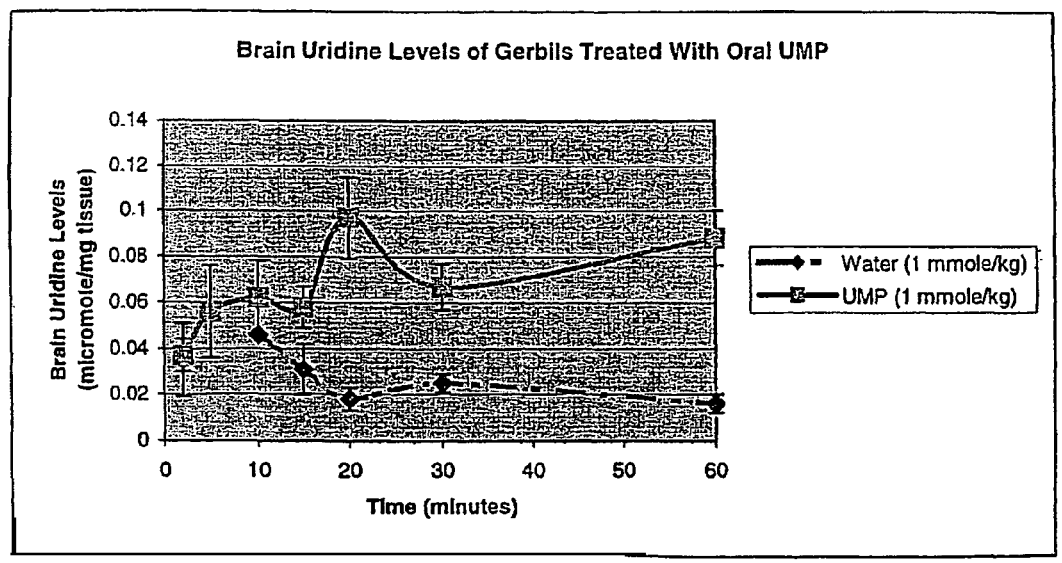
FIG. 8. Oral UMP administration raises brain uridine levels. Depicted are brain uridine levels at various time points following administration or administration of water or UMP.
Figure 9:
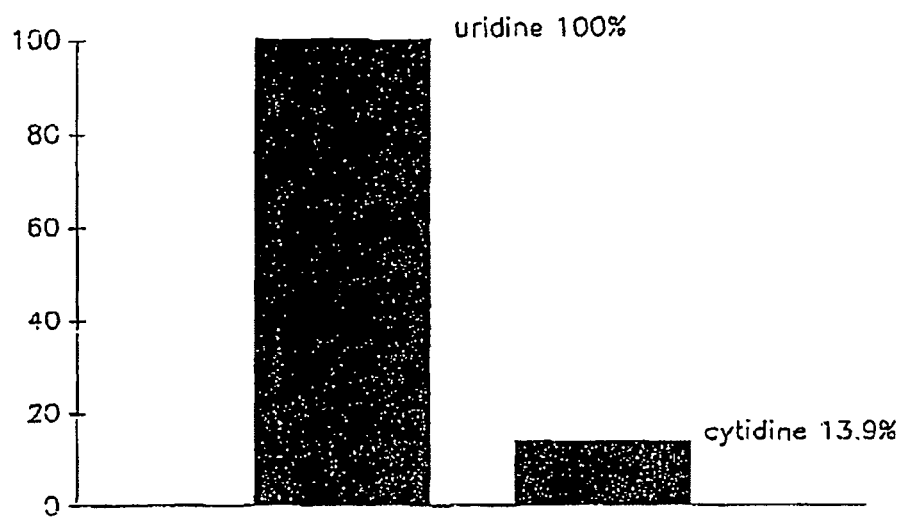
FIG. 9. Uridine is readily converted to cytidine in the brain. Depicted is the ratio of uridine (100%) to cytidine in plasma (A) and in the brain (B) after oral administration of 250 milligram per kg of body weight (mg/kg) of uridine.
Figure 9:
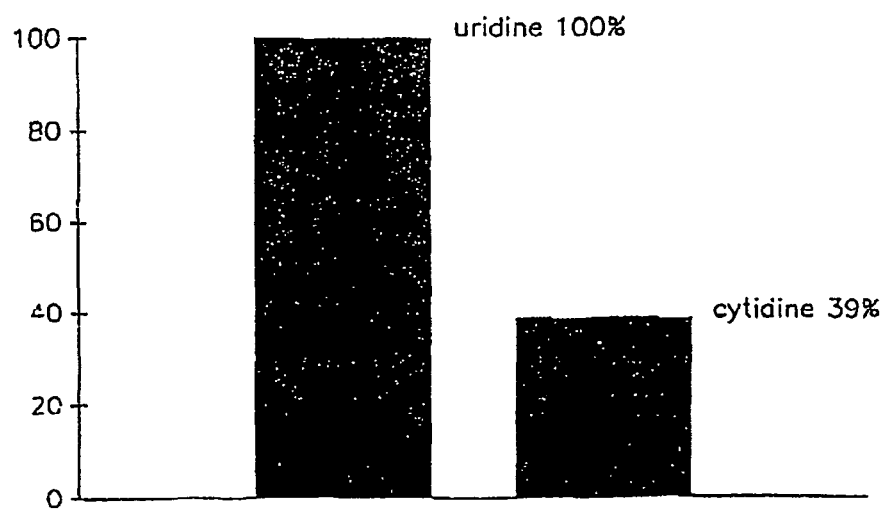
Figure 10:
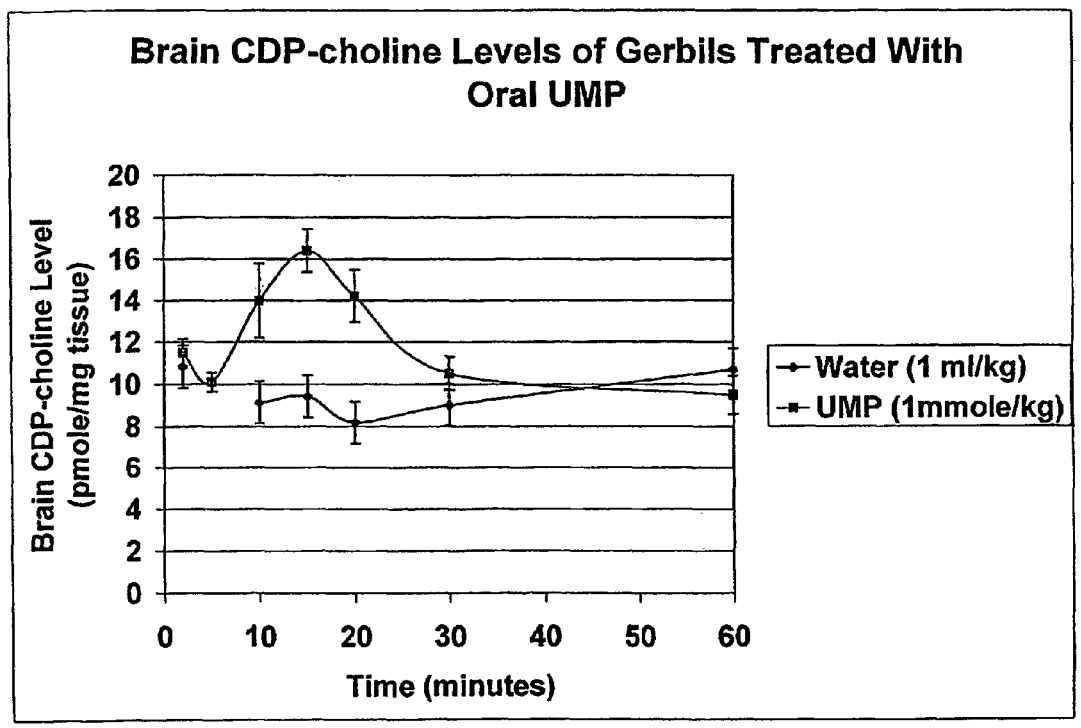
FIG. 10. Oral UMP administration raises brain CDP-choline levels. Depicted are brain CDP-choline levels at various time points following administration or administration of water or UMP.
Figure 11:
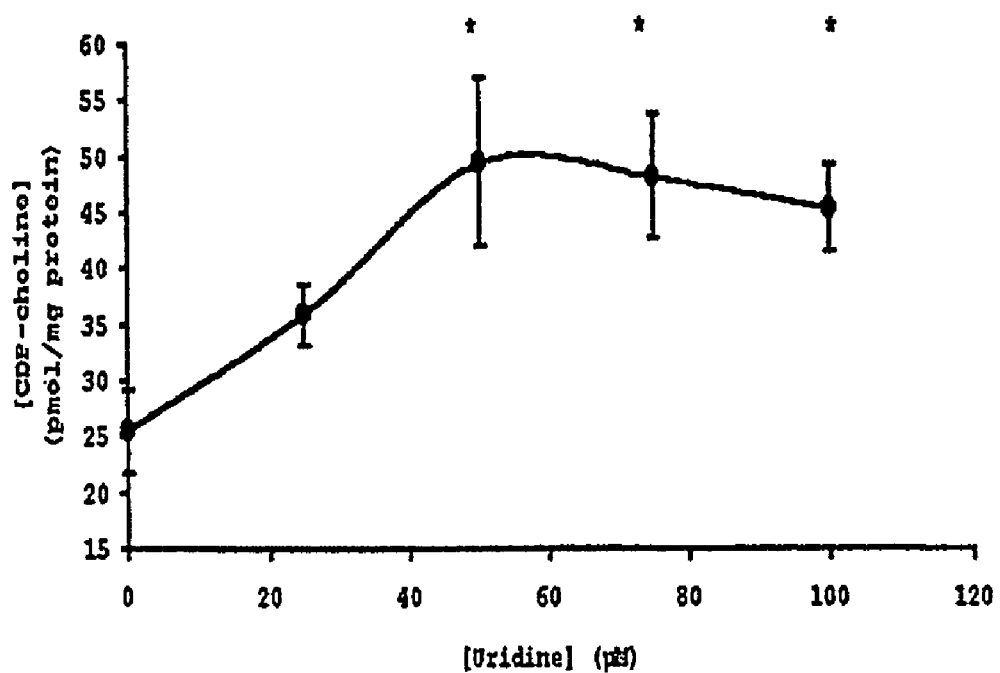
FIG. 11. Uridine increases intracellular levels of CDP-choline in a neural cell line. Cells were incubated for 6 h with the indicated concentrations of uridine. Depicted are the means+/−S.E.M. of six dishes, expressed as picomole (pmol) CDP-choline/mg protein. The experiment was repeated 3 times. *: $p<0.05$.

For example, FIGS. 9-11 show that orally administered uridine acts rapidly and effectively to raise levels of cytidine in the brain. In combination with FIGS. 3-8, which show that uridine is effectively and rapidly absorbed into the bloodstream, in several species, including humans, these findings demonstrate that orally administered uridine is an effective method of raising levels of cytidine and CDP-choline.

The findings of the present invention show that administration of uridine, etc. raises cytidine levels Thus, administering uridine or uridine precursors can be beneficial to human patients in need thereof. However, the potential benefit of uridine or uridine precursor administration is greater than the benefit of cytidine administration. This is due to the fact that cytidine, as opposed to uridine, either cannot cross or is much less efficient than uridine in crossing the blood-brain barrier (Cornford et al., Independent blood-brain barrier transport systems for nucleic acid precursors. Biochim. Biophys. Acta 349:211-219, 1975).

In one embodiment, the cytidine level is a systemic level In another embodiment, the cytidine level is a brain level. In another embodiment, the cytidine level is a nervous system level. Each possibility represents a separate embodiment of the present invention.

In another embodiment, the present invention provides a method of improving or enhancing a neurological function in a subject, comprising administering a uridine, a derivative or metabolite thereof, or a precursor thereof to the subject, thereby improving or enhancing a neurological function in a subject.

In one embodiment, the neurological function is, for example, a synaptic transmission. In one embodiment, the synaptic transmission is adjacent to a motor neuron In another embodiment, the synaptic transmission is adjacent to an interneuron. In one embodiment, the synaptic transmission is adjacent to a sensory neuron. Each type of synaptic transmission represents a separate embodiment of the present invention.

Figure 12:
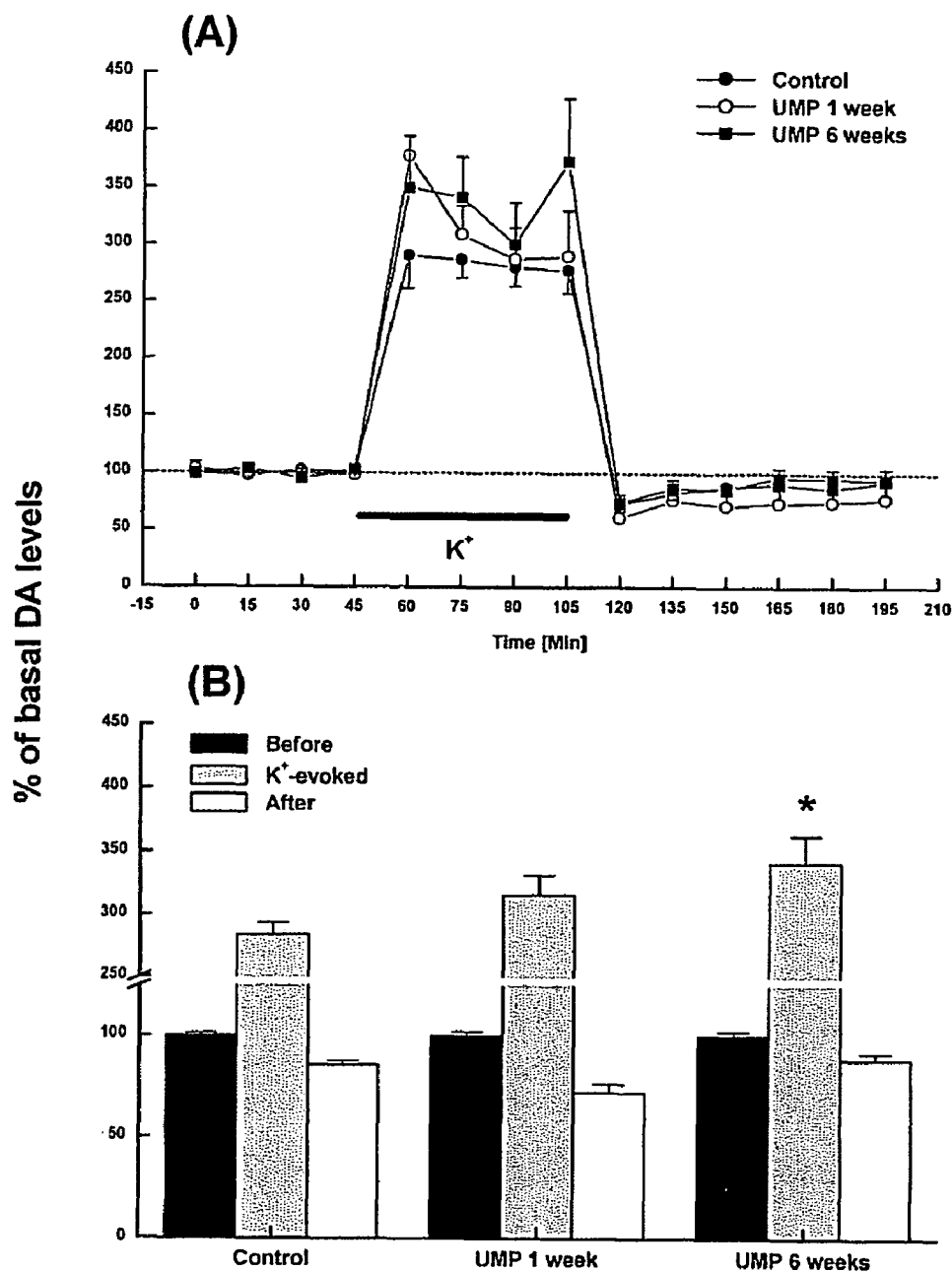
FIG. 12. UMP dietary supplementation significantly increases potassium-evoked dopamine (DA) release in striatal dialysate. (A) Effect of dietary UMP supplementations on $K^+$-evoked striatal DA release. Data were calculated from six to nine measurements at each point (means±standard error of measurement [S.E.M.]). The 100% value represented the mean of the four measurements before potassium stimulation was set at 100%. (B) Data were pooled according to UMP treatment groups. "*" denotes $p<0.05$ compared to corresponding controls.
Figure 13:
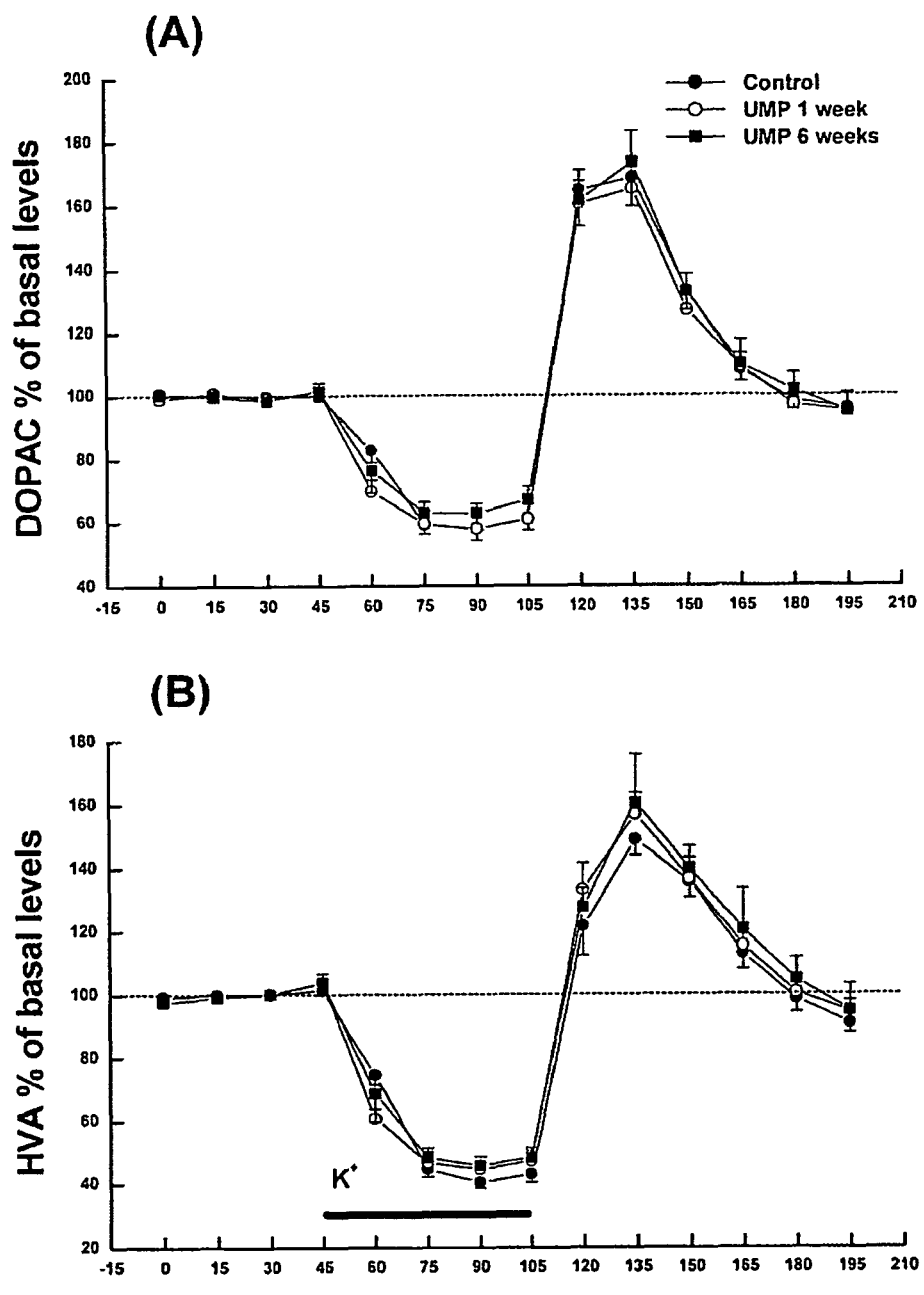
FIG. 13. Effect of potassium on DOPAC and HVA levels in striatal dialysate with UMP dietary supplementation. (A): DOPAC (B): HVA. *: $p<0.05$ compared to corresponding controls.

For example, the data in FIGS. 12-13 show that uridine significantly improves neurotransmitter function, highlighting the ability of uridine to improve neurological function. The data in FIGS. 14-17 show a beneficial effect of uridine on the morphology of neurites, further demonstrating the ability of uridine to improve neurological function.

In another embodiment, improving the synaptic transmission in the subject is achieved by stimulating an amount of a membrane of a neural cell as a result of administration of the uridine, derivative or metabolite thereof, or precursor thereof. In another embodiment improving the synaptic transmission in the subject is achieved by enhancing an amount of a membrane of a neural cell. In another embodiment improving the synaptic transmission in the subject is achieved by stimulating a synthesis of a membrane of a neural cell. In another embodiment improving the synaptic transmission in the subject is achieved by enhancing a synthesis of a membrane of a neural cell. In another embodiment, stimulating or enhancing an amount of or a synthesis of a membrane of a neural cell is partially responsible for mediating improving the synaptic transmission in the subject. In another embodiment, the uridine, derivative or metabolite thereof, or precursor thereof improves the synaptic transmission without stimulating or enhancing an amount of or a synthesis of a membrane of a neural cell. Each possibility represents a separate embodiment of the present invention.

In another embodiment, stimulating an amount of or a synthesis of a membrane of a neural cell is accomplished by stimulating a synthesis of a phospholipid (Example 6). In another embodiment, stimulating or enhancing an amount of or a synthesis of a membrane of a neural cell is accomplished by enhancing a synthesis of a phospholipid. In another embodiment, stimulating or enhancing an amount of or a synthesis of a membrane of a neural cell is accomplished by stimulating a synthesis of a precursor of a phospholipid. In another embodiment, stimulating or enhancing an amount of or a synthesis of a membrane of a neural cell is accomplished by enhancing a synthesis of a precursor of a phospholipid. In another embodiment, stimulating or enhancing a synthesis of a phospholipid or a precursor thereof is partially responsible for stimulating an amount of or a synthesis of a membrane of a neural cell. In another embodiment, the uridine, derivative or metabolite thereof, or precursor thereof stimulates the amount of or a synthesis of a membrane without stimulating or enhancing a synthesis of a phospholipid or a precursor thereof. Each possibility represents a separate embodiment of the present invention.

The principal constituents of mammalian cell membranes are phosphatides, the most abundant of which is phosphatidylcholine (PC). PC biosynthesis is initiated by the phosphorylation of choline to form phosphocholine, which then combines with cytidine triphosphate (CTP) to form 5'-cytidine diphosphocholine (CDP-choline); this compound then reacts with diacylglycerol (DAG) to produce PC. The rate at which cells form PC is affected by the availability of its precursors.

In another embodiment, the phospholipid whose synthesis is enhanced is a phosphatidylcholine. In another embodiment, the phospholipid is a glycerophospholipid. In another embodiment, the phospholipid is a phosphatidic acid. In another embodiment, the phospholipid is a phosphatidylethanolamine. In another embodiment, the phospholipid is a lecithin. In another embodiment, the phospholipid is a phosphatidylinositol. In another embodiment, the phospholipid is a phosphatidylserine. In another embodiment, the phospholipid is a 2-lysolecithin. In another embodiment, the phospholipid is a plasmalogen. In another embodiment, the phospholipid is a choline plasmalogen. In another embodiment, the phospholipid is a phosphatidylglycerol. In another embodiment, the phospholipid is a choline diphosphatidylglycerol. In another embodiment, the phospholipid is a choline sphingolipid. In another embodiment, the phospholipid is a choline sphingomyelin. In another embodiment, the phospholipid is any other phospholipid known in the art. Each type of phospholipid represents a separate embodiment of the present invention.

In another embodiment, the phospholipid precursor is CDP-choline (Example 6). In another embodiment, the phospholipid precursor is CTP. In another embodiment, the phospholipid precursor is inositol. In another embodiment, the phospholipid precursor is choline. In another embodiment, the phospholipid precursor is glycerol. In another embodiment, the phospholipid precursor is acetate. In another embodiment, the phospholipid precursor is any other phospholipid precursor known in the art. Each phospholipid precursor represents a separate embodiment of the present invention.

In another embodiment, the synaptic transmission is improved or enhanced by means of stimulating an outgrowth of a neurite of a neural cell. In another embodiment, the synaptic transmission is improved or enhanced by means of enhancing an outgrowth of a neurite of a neural cell. In another embodiment, stimulating or enhancing an outgrowth of a neurite of a neural cell is partially responsible for is improving or enhancing the synaptic transmission. In another embodiment, uridine, derivative or metabolite thereof, or precursor thereof improves or enhances synaptic transmission without stimulating an outgrowth of a neurite. Each possibility represents a separate embodiment of the present invention.

"Neurite" refers, in one embodiment, to a process growing out of a neuron. In one embodiment, the process is a dendrite. In another embodiment, the process is an axon. Each type of neurite represents a separate embodiment of the present invention.

The data of Example 9 shows that when levels of membrane precursors are increased, neurons produce more neurites, with more branches. By increasing its surface area and size, a cell is able, in one embodiment, to form more connections with neighboring cells. Moreover, an increase in the amount or composition of plasma membrane alters, in one embodiment, neurotransmitter synthesis and release, which also, in one embodiment, affects memory formation. Thus, compounds that promote neurite outgrowth, such as uridine, are useful for treatment of neuro-degenerative disorders like Alzheimer's disease, which involves both loss of neuronal connections and memory impairment.

In another embodiment, the neural cell of the present invention is newly differentiated. In another embodiment, the neural cell is not newly differentiated. In one embodiment, "newly differentiated" refers to a neuron that has differentiated in the 24 hours prior to commencing administration of the uridine, derivative or metabolite thereof, or precursor thereof In another embodiment, "newly differentiated" refers to a neuron that has differentiated in the 48 hours prior to commencing administration of the uridine, derivative or metabolite thereof, or precursor thereof. In another embodiment, "newly differentiated" refers to a neuron that has differentiated in the 72 hours prior to commencing administration of the uridine, derivative or metabolite thereof, or precursor thereof. In another embodiment, "newly differentiated" refers to a neuron that has differentiated in the 1 week prior to commencing administration of the uridine, derivative or metabolite thereof, or precursor thereof. In another embodiment, "newly differentiated" refers to a neuron that completes its differentiation following commencement of administration of the uridine, derivative or metabolite thereof, or precursor thereof. Each possibility represents a separate embodiment of the present invention.

Methods of assessing neuronal differentiation are well known in the art, and are described, for example, in Contestabile A et al (Neurochem Int. 45: 903-14, 2004). Each such method represents a separate embodiment of the present invention.

In another embodiment, the synaptic transmission is improved or enhanced by increasing the number of neurites of the neural cell (Example 9). In another embodiment, improvement or enhancement of the synaptic transmission occurs without increasing the number of neurites of the neural cell. Each possibility represents a separate embodiment of the present invention.

In another embodiment, the synaptic transmission is improved or enhanced by stimulating branching of a neurite of a neural cell (Example 9). In another embodiment, the synaptic transmission is improved or enhanced by enhancing branching of a neurite of a neural cell. In another embodiment, improvement or enhancement of the synaptic transmission occurs without stimulating or enhancing branching of a neurite of a neural cell. Each possibility represents a separate embodiment of the present invention.

In another embodiment, one of the above effects upon a neural cell is stimulated or enhanced by means of stimulating a P2Y receptor in the neural cell. In another embodiment, one of the above effects upon a neural cell is stimulated or enhanced partially as a result of stimulating a P2Y receptor in the neural cell. In another embodiment, one of the above effects upon a neural cell is stimulated or enhanced without stimulating a P2Y receptor in the neural cell. Each possibility represents a separate embodiment of the present invention.

P2Y receptors are a family of receptors known to be involved in platelet activation and other biological functions. They are reviewed in Mahaut-Smith M P et al, Platelets. 2004 15:131-44, 2004.

In one embodiment, the P2Y receptor of the present invention is a P2Y2 receptor. In another embodiment, the P2Y receptor is a P2Y4 receptor. In another embodiment, the P2Y receptor is a P2Y6 receptor. In another embodiment, the P2Y receptor is any other P2Y receptor known in the art. Each possibility represents a separate embodiment of the present invention.

In another embodiment, the neurological function that is improved or enhanced is a function of a neurotransmitter. In one embodiment, improving or enhancing a function of a neurotransmitter occurs by means of increasing a level of the neurotransmitter in a synapse. In another embodiment, improving or enhancing a function of a neurotransmitter occurs by means of increasing the release of the neurotransmitter into a synapse. In another embodiment, improving or enhancing a function of a neurotransmitter occurs without changing the level or release of the neurotransmitter in a synapse. Each possibility represents a separate embodiment of the present invention.

In one embodiment, the neurotransmitter is dopamine. In another embodiment, the neurotransmitted is acetylcholine. In another embodiment, the neurotransmitter is Serotonin. In another embodiment, the neurotransmitter is 5-Hydroxytryptamine (5-HT). In another embodiment, the neurotransmitter is GABA. In another embodiment, the neurotransmitter is any other neurotransmitter known in the art. Each type of neurotransmitter represents a separate embodiment of the present invention.

Dopamine is classified as a catecholamine (a class of molecules that serve as neurotransmitters and hormones). It is a monoamine, meaning that it has a single amine group.

Measurement of DA release during depolarization in rat striatum is well known in the art (see, for example, Ripley T L et al, J Neurosci Methods. 78: 7-14, 1997; Zetterstrom T et al, Eur J Pharmacol. 148: 327-334, 1988). The magnitude of depolarization increases DA release in a dose-dependent fashion.

In one embodiment, release of the neurotransmitter following a stimulation of a neuron adjacent to the synapse is improved or enhanced. In another embodiment, basal level release of the neurotransmitter is improved or enhanced. Each possibility represents a separate embodiment of the present invention.

In one embodiment, the stimulation of the neuron comprises exposure of the neuron to a potassium ion. In another embodiment, the stimulation of the neuron comprises any other means of neural stimulation known in the art. Methods for assessing neural stimulation and release of neurotransmitters are well known in the art, and are described, for example, in Bewick G S, J Neurocytol. 32: 473-87, 2003. Each possibility represents a separate embodiment of the present invention.

In another embodiment, one of the above affects on cognitive function or neurological function is achieved by increasing a level of cytidine, cytidine triphosphate, CDP-choline, or a derivative or metabolite thereof in the subject. In another embodiment, improving or enhancing a neurological function in a subject is achieved without increasing a level of a cytidine, a cytidine triphosphate, a CDP-choline, or a derivative or metabolite thereof in the subject. Each possibility represents a separate embodiment of the present invention.

In another embodiment, the present invention provides a method of increasing a level of a cytidine, a cytidine triphosphate, a CDP-choline, or a derivative or metabolite thereof in a tissue or plasma of a subject, comprising administering a uridine, a derivative or metabolite thereof, or a precursor thereof to the subject, thereby increasing a level of a cytidine, a cytidine triphosphate, a CDP-choline, or a derivative or metabolite thereof in a tissue or plasma of a subject.

In one embodiment, the tissue is a brain tissue. In one embodiment, the tissue is a neural tissue. In another embodiment, the tissue is a spinal tissue. In another embodiment, the tissue is any other tissue known in the art. Each possibility represents a separate embodiment of the present invention.

In another embodiment, the present invention provides a method of stimulating or enhancing an amount of or a synthesis of a component of a membrane of a cell, comprising contacting the cell with a uridine or a derivative or metabolite thereof, thereby stimulating or enhancing an amount of or a synthesis of a membrane of a cell. In one embodiment, the cell is a neural cell. In another embodiment, the cell is a brain cell. In another embodiment, the cell is any cell in which synthesis of a membrane or a component thereof is enhanced by contact with uridine or a derivative or metabolite thereof. Each possibility represents a separate embodiment of the present invention.

In one embodiment, stimulating or enhancing the synthesis of the cell membrane is achieved by stimulating a synthesis of a phospholipid. In another embodiment, stimulating or enhancing the synthesis of the cell membrane is achieved by enhancing a synthesis of a phospholipid. In another embodiment, stimulating or enhancing the synthesis of the cell membrane is achieved by stimulating a synthesis of a phospholipid precursor. In another embodiment, enhancing the synthesis of the cell membrane is achieved by stimulating or enhancing a synthesis of a phospholipid precursor. In another embodiment, stimulating or enhancing the synthesis of the cell membrane is achieved without stimulating or enhancing the synthesis of the cell membrane. Each possibility represents a separate embodiment of the present invention.

In another embodiment, the present invention provides a method of stimulating or enhancing an outgrowth of a neurite of a neural cell, comprising contacting the neural cell with a uridine or a derivative or metabolite thereof, thereby stimulating or enhancing an outgrowth of a neurite of a neural cell.

In another embodiment, stimulation or enhancing an outgrowth of a neurite of a neural cell is achieved by stimulation of a P2Y receptor in the neural cell.

In another embodiment, the present invention provides a method of increasing a number of neurites of a neural cell, comprising contacting the neural cell with a uridine or a derivative or metabolite thereof, thereby increasing a number of neurites of a neural cell.

In another embodiment, the present invention provides a method of stimulating or enhancing a branching of a neurite of a neural cell, comprising contacting the neural cell with a uridine or a derivative or metabolite thereof, thereby stimulating or enhancing a branching of a neurite of a neural cell.

In one embodiment, one of the above effects is achieved by stimulating a P2Y receptor in the neural cell. In one embodiment, the effect is achieved without stimulating a P2Y receptor in the neural cell. Each possibility represents a separate embodiment of the present invention.

In another embodiment, the present invention provides a method of stimulating or enhancing production of a membrane of a brain cell of a subject, comprising administering to the subject a uridine, whereby the uridine stimulates a P2Y receptor in the brain cell, thereby stimulating or enhancing production of a membrane of a brain cell of a subject. In another embodiment, the present invention provides a method of stimulating or enhancing production of a membrane of a brain cell of a subject, comprising administering to the subject a uridine derivative, whereby the uridine derivative stimulates a P2Y receptor in the brain cell, thereby stimulating or enhancing production of a membrane of a brain cell of a subject. In another embodiment, the present invention provides a method of stimulating or enhancing production of a membrane of a brain cell of a subject, comprising administering to the subject a uridine metabolite, whereby the uridine metabolite stimulates a P2Y receptor in the brain cell, thereby stimulating or enhancing production of a membrane of a brain cell of a subject.

In another embodiment, the brain cell of the present invention is newly differentiated. In another embodiment, the brain cell is not newly differentiated. Each possibility represents a separate embodiment of the present invention.

In another embodiment, the present invention provides a method of stimulating or enhancing production of a membrane of a neural cell of a subject, comprising administering to the subject a uridine, whereby the uridine stimulates a P2Y receptor in the neural cell, thereby stimulating or enhancing production of a membrane of a neural cell of a subject In another embodiment, the present invention provides a method of stimulating or enhancing production of a membrane of a neural cell of a subject, comprising administering to the subject a uridine derivative, whereby the uridine derivative stimulates a P2Y receptor in the neural cell. In another embodiment, the present invention provides a method of stimulating or enhancing production of a membrane of a neural cell of a subject, comprising administering to the subject a uridine metabolite, whereby the uridine metabolite stimulates a P2Y receptor in the neural cell.

In another embodiment, the present invention provides a method of stimulating or enhancing production of a membrane of a brain cell of a subject, comprising administering to the subject a uridine, whereby the uridine is converted to a second compound that stimulates a P2Y receptor in the brain cell, thereby stimulating or enhancing production of a membrane of a brain cell of a subject. In another embodiment, the present invention provides a method of stimulating or enhancing production of a membrane of a brain cell of a subject, comprising administering to the subject a uridine derivative, whereby the uridine derivative is converted to a second compound that stimulates a P2Y receptor in the brain cell. In another embodiment, the present invention provides a method of stimulating or enhancing production of a membrane of a brain cell of a subject, comprising administering to the subject a uridine metabolite, whereby the uridine metabolite is converted to a second compound that stimulates a P2Y receptor in the brain cell.

In another embodiment, the present invention provides a method of stimulating or enhancing production of a membrane of a neural cell of a subject, comprising administering to the subject a uridine, whereby the uridine is converted to a second compound that stimulates a P2Y receptor in the neural cell, thereby stimulating or enhancing production of a membrane of a neural cell of a subject. In another embodiment, the present invention provides a method of stimulating or enhancing production of a membrane of a neural cell of a subject, comprising administering to the subject a uridine derivative, whereby the uridine derivative is converted to a second compound that stimulates a P2Y receptor in the neural cell. In another embodiment, the present invention provides a method of stimulating or enhancing production of a membrane of a neural cell of a subject, comprising administering to the subject a uridine metabolite, whereby the uridine metabolite is converted to a second compound that stimulates a P2Y receptor in the neural cell.

In another embodiment, the present invention provides a method of stimulating or enhancing production of a membrane of a brain cell, comprising contacting the brain cell with a uridine, whereby the uridine stimulates a P2Y receptor in the brain cell, thereby stimulating or enhancing production of a membrane of a brain cell. In another embodiment, the present invention provides a method of stimulating or enhancing production of a membrane of a brain cell, comprising contacting the brain cell with a uridine derivative, whereby the uridine derivative stimulates a P2Y receptor in the brain cell, thereby stimulating or enhancing production of a membrane of a brain cell. In another embodiment, the present invention provides a method of stimulating or enhancing production of a membrane of a brain cell, comprising contacting the brain cell with a uridine metabolite, whereby the uridine metabolite stimulates a P2Y receptor in the brain cell, thereby stimulating or enhancing production of a membrane of a brain cell.

In another embodiment, the present invention provides a method of stimulating or enhancing production of a membrane of a neural cell, comprising contacting the neural cell with a uridine, whereby the uridine stimulates a P2Y receptor in the neural cell, thereby stimulating or enhancing production of a membrane of a neural cell. In another embodiment, the present invention provides a method of stimulating or enhancing production of a membrane of a neural cell, comprising contacting the neural cell with a uridine derivative, whereby the uridine derivative stimulates a P2Y receptor in the neural cell. In another embodiment, the present invention provides a method of stimulating or enhancing production of a membrane of a neural cell, comprising contacting the neural cell with a uridine metabolite, whereby the uridine metabolite stimulates a P2Y receptor in the neural cell.

In another embodiment, the present invention provides a method of stimulating or enhancing production of a membrane of a brain cell, comprising contacting the brain cell with a uridine, whereby the uridine is converted to a second compound that stimulates a P2Y receptor in the brain cell, thereby stimulating or enhancing production of a membrane of a brain cell. In another embodiment, the present invention provides a method of stimulating or enhancing production of a membrane of a brain cell, comprising contacting the brain cell with a uridine derivative, whereby the uridine derivative is converted to a second compound that stimulates a P2Y receptor in the brain cell. In another embodiment, the present invention provides a method of stimulating or enhancing production of a membrane of a brain cell, comprising contacting the brain cell with a uridine metabolite, whereby the uridine metabolite is converted to a second compound that stimulates a P2Y receptor in the brain cell.

In one embodiment, the second compound is uridine-5'-triphosphate. In another embodiment, the second compound is any metabolic product known in the art of uridine or derivative or metabolite thereof. Each compound represents a separate embodiment of the present invention.

In one embodiment, the uridine or derivative or metabolite thereof is converted into the second compound intracellularly. In another embodiment, the uridine or derivative or metabolite thereof is converted into the second compound extracellularly. In another embodiment, the uridine or derivative or metabolite thereof is secreted from a cell after being converted into the second compound. In another embodiment, the uridine or derivative or metabolite thereof contacts a different cell after being secreted from the cell in which it was converted to the second compound, and stimulates a P2Y receptor in the different cell. Each possibility represents a separate embodiment of the present invention.

In another embodiment, the present invention provides a method of stimulating or enhancing production of a membrane of a neural cell, comprising contacting the neural cell with a uridine, whereby the uridine is converted to a second compound that stimulates a P2Y receptor in the neural cell, thereby stimulating or enhancing production of a membrane of a neural cell. In another embodiment, the present invention provides a method of stimulating or enhancing production of a membrane of a neural cell, comprising contacting the neural cell with a uridine derivative, whereby the uridine derivative is converted to a second compound that stimulates a P2Y receptor in the neural cell. In another embodiment, the present invention provides a method of stimulating or enhancing production of a membrane of a neural cell, comprising contacting the neural cell with a uridine metabolite, whereby the uridine metabolite is converted to a second compound that stimulates a P2Y receptor in the neural cell.

In another embodiment, the present invention provides a method of stimulating or enhancing synthesis of a membrane component of a brain cell of a subject, comprising administering to the subject a uridine or a derivative or metabolite thereof, whereby the uridine or derivative or metabolite thereof stimulates a P2Y receptor in the brain cell, thereby stimulating or enhancing synthesis of a membrane component of a brain cell of a subject. In another embodiment, the present invention provides a method of stimulating or enhancing synthesis of a membrane component of a neural cell of a subject, comprising administering to the subject a uridine or a derivative or metabolite thereof, whereby the uridine or derivative or metabolite thereof stimulates a P2Y receptor in the neural cell, thereby stimulating or enhancing synthesis of a membrane component of a neural cell of a subject.

In another embodiment, the present invention provides a method of stimulating or enhancing synthesis of a membrane component of a brain cell of a subject, comprising administering to the subject a uridine or a derivative or metabolite thereof, whereby the uridine or derivative or metabolite thereof is converted to a second compound that stimulates a P2Y receptor in the brain cell, thereby stimulating or enhancing synthesis of a membrane component of a brain cell of a subject. In another embodiment, the present invention provides a method of stimulating or enhancing synthesis of a membrane component of a neural cell of a subject, comprising administering to the subject a uridine or a derivative or metabolite thereof, whereby the uridine or derivative or metabolite thereof is converted to a second compound that stimulates a P2Y receptor in the neural cell, thereby stimulating or enhancing synthesis of a membrane component of a neural cell of a subject.

In one embodiment, the membrane is a neurite membrane. In another embodiment, the membrane is a dendritic membrane. In another embodiment, the membrane is a dendritic membrane. In another embodiment, the membrane is any other type of membrane known in the art. Each type of membrane represents a separate embodiment of the present invention.

In one embodiment, the P2Y receptor is a P2Y2 receptor. In another embodiment, the P2Y receptor is a P2Y4 receptor. In another embodiment, the P2Y receptor is a P2Y4 receptor. In another embodiment, the P2Y receptor is any other P2Y receptor known in the art. In another embodiment, the P2Y receptor is a combination of a number of P2Y receptors. Each possibility represents a separate embodiment of the present invention.

In one embodiment of the methods of the present invention, the uridine or derivative or metabolite thereof is carried in the subjects' bloodstream to the subject's brain cell or neural cell. In another embodiment, the uridine or derivative or metabolite thereof is carried by diffusion to the subject's brain cell or neural cell. In another embodiment, the uridine or derivative or metabolite thereof is carried by active transport to the subject's brain cell or neural cell. In another embodiment, the uridine or derivative or metabolite thereof is administered to the subject in such a way that it directly contacts the subject's brain cell or neural cell. Each possibility represents a separate embodiment of the present invention.

Each method of stimulating or enhancing production of a membrane of a neural cell of a subject, method of stimulating or enhancing production of a membrane of a brain cell of a subject, method of stimulating or enhancing production of a membrane component of a neural cell of a subject, and method of stimulating or enhancing production of a membrane component of a brain cell of a subject, described herein represents a separate embodiment of the present invention.

Methods for assessing production of a brain cell membrane or neural cell membrane are well known in art. In one embodiment, membrane production is assessed by measuring the level of neurite outgrowth (Example 11). In another embodiment, membrane production is assessed by measuring the level of neurite outgrowth (Example 9). In another embodiment, membrane production is assessed by measuring the level of a membrane marker protein (Example 8). In another embodiment, membrane production is assessed by measuring synthesis of a membrane precursor. In another embodiment, membrane production is assessed by measuring amounts of membrane prior to and following uridine treatment. In another embodiment, membrane production is assessed by measuring biological indicators of membrane turnover. Indicators or cellular membrane turnover are well known in the art, and are described, for example, in Das K P et al, Neurotoxicol Teratol 26(3): 397-406, 2004. Each method of assessing membrane production represents a separate embodiment of the present invention.

In one embodiment, the P2Y receptor stimulates a second messenger. In one embodiment, the second messenger is a G alpha protein. In another embodiment, the second messenger is a G alpha(q) protein. In another embodiment, the second messenger is cAMP. In another embodiment, the second messenger is any other second messenger known in the art. Second messengers, and their associated signaling pathways, are well known in the art, and are described, for example, in Ferguson S, Pharm Rev 53: 1-24, 2001; Huang E et al, Ann Rev Biochem 72: 609-642, 2003; and Blitterswijk W et al, Biochem. J. 369: 199-211, 2003. Each second messenger represents a separate embodiment of the present invention.

In another embodiment, the second messenger stimulates a phospholipase C enzyme. In another embodiment, the second messenger modulates intracellular calcium levels. In another embodiment, the second messenger increases protein kinase C activity. In one embodiment, one or more of the above pathways stimulates membrane production. In another embodiment, the second messenger modulates or stimulates another cellular pathway that stimulates membrane production. Each possibility represents a separate embodiment of the present invention.

In another embodiment, the present invention provides a method of increasing the number of neurites of a brain cell or a neural cell, comprising contacting the cells with a uridine or a derivative or metabolite thereof, whereby the uridine or derivative or metabolite thereof stimulates a P2Y receptor in the brain cell, thereby increasing the number of neurites of a brain cell or a neural cell.

In another embodiment, the present invention provides a method of stimulating or enhancing branching of a neurite of a neural cell or a brain cell, comprising contacting the cells with a uridine or a derivative or metabolite thereof, whereby the uridine or derivative or metabolite thereof stimulates a P2Y receptor in the brain cell, thereby stimulating or enhancing branching of a neurite of a neural cell or a brain cell.

In another embodiment, the present invention provides a method of increasing a level of a neurotransmitter in a synapse of a neural cell or a brain cell, comprising contacting the cells with a uridine or a derivative or metabolite thereof, whereby the uridine or derivative or metabolite thereof stimulates a P2Y receptor in the brain cell, thereby increasing a level of a neurotransmitter in a synapse of a neural cell or a brain cell.

In another embodiment, the present invention provides a method of increasing the release of a neurotransmitter into a synapse of a brain cell or a neural cell, comprising contacting the cells with a uridine or a derivative or metabolite thereof, whereby the uridine or derivative or metabolite thereof stimulates a P2Y receptor in the brain cell, thereby increasing the release of a neurotransmitter into a synapse of a brain cell or a neural cell.

In another embodiment, the present invention provides a method of increasing the sensitivity of a neuron or a brain cell to a stimulus, comprising contacting the cells with a uridine or a derivative or metabolite thereof, whereby the uridine or derivative or metabolite thereof stimulates a P2Y receptor in the brain cell, increasing the sensitivity of a neuron or a brain cell to a stimulus.

In another embodiment, the present invention provides a method of increasing a level of a neurotransmitter in a synapse, comprising contacting a neural cell adjacent to the synapse with a uridine or a derivative or metabolite thereof, thereby increasing a level of the neurotransmitter in a synapse.

In another embodiment, the present invention provides a method of increasing a release of a neurotransmitter into a synapse, comprising contacting a neural cell adjacent to the synapse with a uridine or a derivative or metabolite thereof, thereby increasing a release of the neurotransmitter into a synapse.

In one embodiment, the neurotransmitter is dopamine. In another embodiment, the neurotransmitter is any other neurotransmitter known in the art. Each possibility represents a separate embodiment of the present invention.

In another embodiment, the present invention provides a method of increasing a sensitivity of a neuron to a stimulus, comprising contacting the neuron with a uridine or a derivative or metabolite thereof, thereby increasing a sensitivity of a neuron to a stimulus.

In another embodiment, the release that is stimulated occurs following a stimulation of a neuron adjacent to the synapse. In another embodiment, the release that is stimulated is basal release. In one embodiment, the stimulation comprises exposure of the neuron to a potassium ion. In one embodiment, the stimulation is any other means of neural stimulation known in the art. Each possibility represents a separate embodiment of the present invention.

Gerbils rather than rats or other rodents were selected for some of the experiments in the present invention, as the pyrimidine metabolism of said gerbils is closer to humans. Those skilled in the art generally recognize that the gerbil model is equivalent to a human model. Indeed, gerbils are the choice model for certain human diseases and brain disorders such as cerebral ischemia (Ginsburg et al., Rodent models of cerebral ischemia. Stroke 20: 1627-1642, 1989).

In one embodiment, therapeutically or pharmacologically effective doses of uridine are also doses that produce blood or brain levels of cytidine ranging between 0.1 micromole ($\mu M$) and 1 millimole (mM). In another embodiment, therapeutically or pharmacologically effective doses are doses which produce a desired effect in at least 10% of treated patients population.

In another embodiment, the pharmacologically effective doses are within about 20 mg and 50 g/day range. In another embodiment, the doses are between about 100 mg and 10 g/day. Doses are administered, in one embodiment, either as a single dose or divided in several doses, e.g., 10 mg to 1 g/cap or tab. The minimal duration of the therapy is at least one day but longer periods of time are usually required according to the exigency of the therapy. If needed, the usual time period spans from one day to the period of lifetime. When these compounds are not available in pure form the active ingredient comprises at least about 20-30 percent of the weight of the preparation. The clinical study is continued for at least 1 day or longer as required by the exigencies of the therapy. The dose administered, the frequency of administration and the duration of the treatment will vary, in one embodiment, as a function of the condition of the patient and is determined according to standard clinical procedures known to the practitioner skilled in the relevant art.

In one embodiment, "pharmaceutical composition" means a "therapeutically effective amount" of the active ingredient, i.e. the uridine or derivative or metabolite thereof, together with a pharmaceutically acceptable carrier or diluent. A "therapeutically effective amount" as used herein refers to that amount which provides a therapeutic effect for a given condition and administration regimen.

The pharmaceutical composition containing the uridine or derivative or metabolite thereof is, in one embodiment, administered to a subject by any method known to a person skilled in the art, such as parenterally, paracancerally, transmucosally, transdermally, intramuscularly, intravenously, intradermally, subcutaneously, intraperitonealy, intraventricularly, intracranially, intravaginally or intratumorally.

In another embodiment, the pharmaceutical compositions are administered orally, and thus is formulated in a form suitable for oral administration, i.e. as a solid or a liquid preparation. Suitable solid oral formulations include, for example, tablets, capsules, pills, granules, pellets and the like. Suitable liquid oral formulations include solutions, suspensions, dispersions, emulsions, oils and the like. In one embodiment of the present invention, the uridine or derivative or metabolite thereof is formulated in a capsule. In accordance with this embodiment, the compositions of the present invention comprises, in addition to the uridine or derivative or metabolite thereof active compound and the inert carrier or diluent, a hard gelating capsule.

In another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

In another embodiment, the pharmaceutical compositions are administered topically to body surfaces, and thus are formulated in a form suitable for topical administration. Suitable topical formulations include gels, ointments, creams, lotions, drops and the like. For topical administration, the uridine or derivative or metabolite thereof s or their physiologically tolerated derivatives such as salts, esters, N-oxides, and the like is prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of uridine or derivative or metabolite thereof over a period of time.

Pharmaceutically acceptable carriers or diluents are well known to those skilled in the art. The carrier or diluent is, in one embodiment, a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

For liquid formulations, pharmaceutically acceptable carriers are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In another embodiment, the compositions further comprise binders (e.g. acacia, cornstarch, gelatin, carbomer, ethyl cellulose, guar gum, hydroxypropyl cellulose, hydroxypropyl methyl cellulose, povidone), disintegrating s (e.g. cornstarch, potato starch, alginic acid, silicon dioxide, croscarmelose sodium, crospovidone, guar gum, sodium starch glycolate), buffers (e.g., Tris-HCI, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizers (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing s (e.g. carbomer, colloidal silicon dioxide, ethyl cellulose, guar gum), sweetners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming s (e.g. ethyl cellulose, acrylates, polymethacrylates) and/or adjuvants.

In one embodiment, the pharmaceutical compositions provided herein are controlled release compositions, i.e. compositions in which the uridine or derivative or metabolite thereof is released over a period of time after administration. Controlled or sustained release compositions include formulation in lipophilic depots (e.g. fatty acids, waxes, oils). In another embodiment, the composition is an immediate release composition, i.e. a composition in which all of the uridine or derivative or metabolite thereof is released immediately after administration.

In another embodiment, the pharmaceutical composition can be delivered in a controlled release system. For example, the composition is administered using intravenous infusion, an implantable osmotic pump, a transdermal patch, liposomes, or other modes of administration. In one embodiment, a pump is used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138(1984). Other controlled release systems are discussed in the review by Langer (Science 249:1527-1533 (1990).

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the uridine or derivative or metabolite thereof s or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the uridine or derivative or metabolite thereof s or their physiologically tolerated derivatives such as salts, esters, N-oxides, and the like are converted into a solution, suspension, or emulsion, if desired with the substances customary and suitable for this purpose, for example, solubilizers or other.

An active component can be formulated into the composition as neutralized pharmaceutically acceptable salt forms Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the uridine or derivative or metabolite thereof will be pharmaceutically acceptable salts. Other salts are, in one embodiment, useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

Example 1

Measurement of Cytidine by HPLC Without Interference from Tyrosine

Materials and Methods

Sample Preparation 1-milliliter (mL) samples of heparinized plasma were spiked with 1 µg fluoro-uridine for use as an internal standard, then deproteinized by adding methanol (5 mL). Samples were centrifuged, lyophilized, reconstituted in 5 mL of 0.25 N ammonium acetate (pH 8.8), then immediately purified over boronate affinity columns.

Boronate Affinity Columns

All steps were performed at 4° C. Boronate affinity columns (Affigel-601, Bio-Rad) were primed with two 5-mL ammonium acetate washes, samples were applied, and columns were washed again with ammonium acetate, after which the nucleosides were eluted with 0.1 N formic acid (7 mL). Eluates were lyophilized, then reconstituted in 100 µL water for HPLC analysis. Boronate affinity columns bind many biological molecules, including the nucleotide bases adenosine, cytidine, guanosine, thymidine, and uridine.

HPLC

HPLC analysis was performed using a Beckman System Gold apparatus (Beckman Instruments) equipped with a Rainin Dynamax Microsorb C18 column (3 µm packing; 4.6× 100 mm) at room temperature. The standard HPLC method is described in Lopez-Coviella et al, (J. Neurochem 65: 889-894, 1995). For modified HPLC, an isocratic elution buffer was used containing 0.004 N potassium phosphate buffer (pH 5.8) and 0.1% methanol instead of formic acid, flowing at 1 mL/min and heated to 35°.

Results

Figure 1:
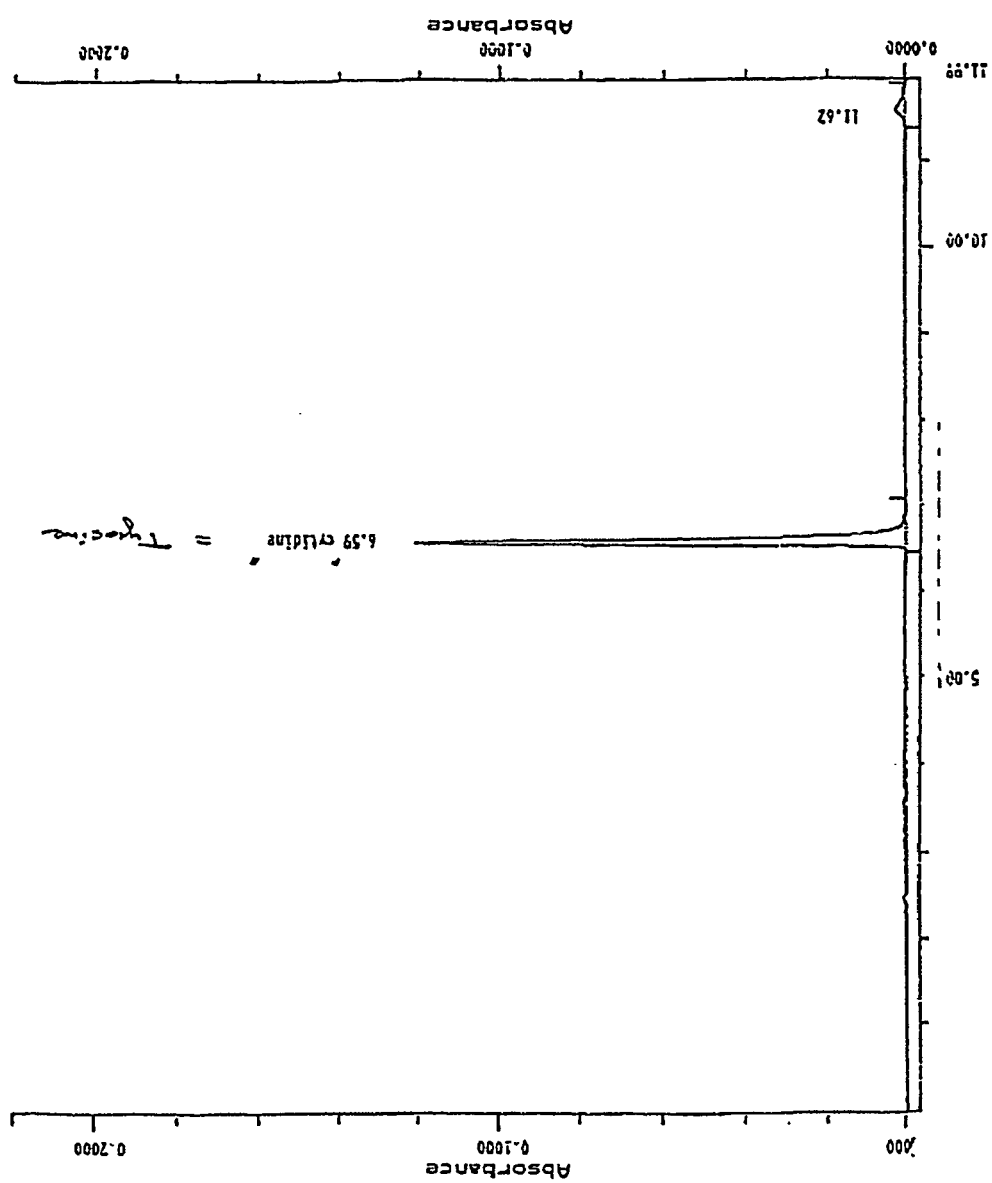
FIG. 1 illustrates the coincidence of cytidine and tyrosine peaks (6.59) when tested by a standard HPLC method.
Figure 2:
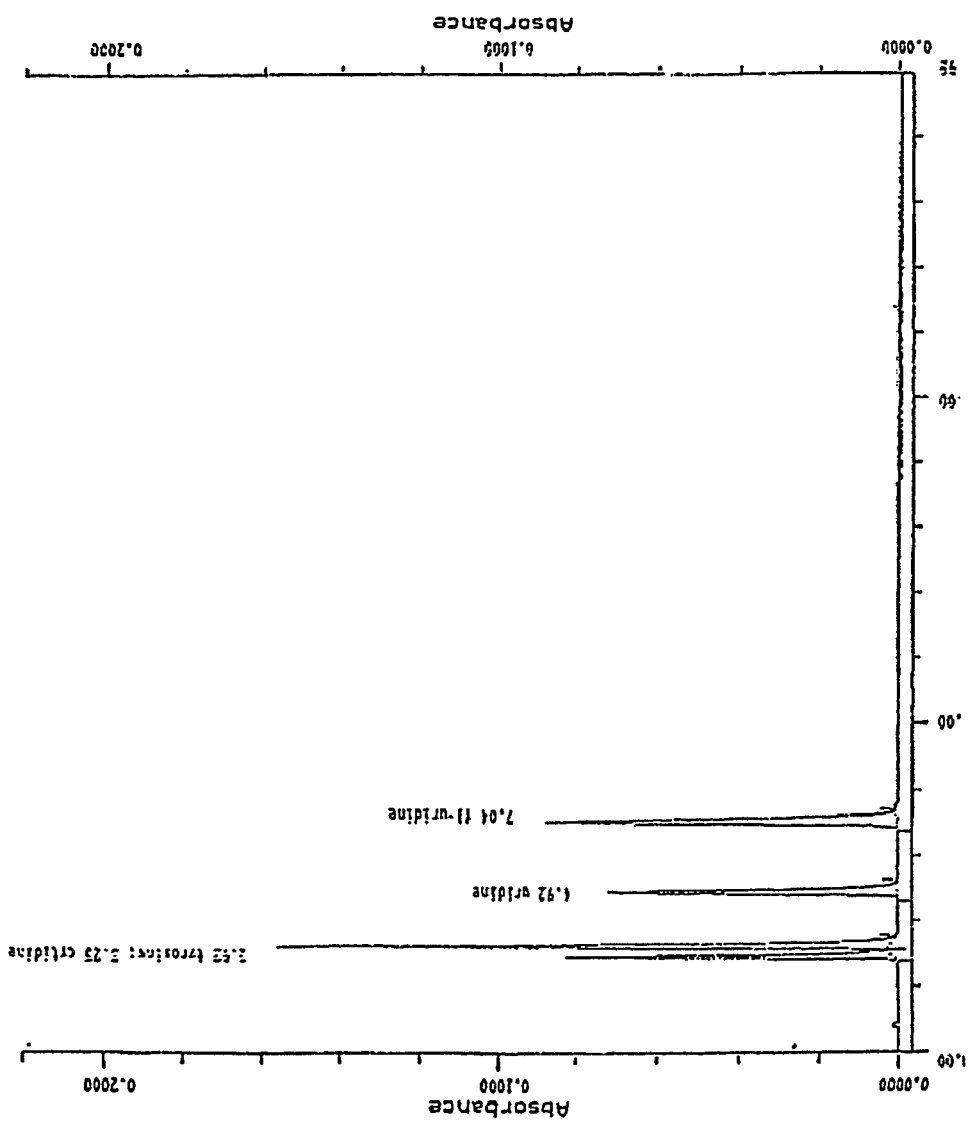
FIG. 2 illustrates distinct cytidine (3.25) and tyrosine (2.92) peaks when tested by a modified HPLC method, which utilizes elution buffer with low methanol.

A standard HPLC method for measuring nucleosides yields separate peaks for uridine and cytidine; however, a coincidence of the cytidine and tyrosine peaks precludes accurate measurement of cytidine levels, as shown for human plasma samples (FIG. 1). Tyrosine is present in many biological fluids, e.g., plasma or cerebiospinal fluid (CSF). In the present Example, a modified HPLC method was used which distinguished cytidine and tyrosine peaks, permitting accurate measurement of cytidine levels (FIG. 2).

Example 2

Oral Administration of UMP Increases Plasma Uridine Levels in Humans

Methods

Study Design

Eight healthy subjects (5 male, 3 female, 27-67 years old) were instructed to fast overnight and given sequentially increasing doses (500, 1000, and 2000 mg) of disodium UMP (Numico, Wageningen, NL) at 7-8 AM on each of three days, separated by at least a three-day washout period. All subjects were given lunch. Blood samples were drawn over an eight-hour period into heparinized tubes. Plasma was treated with methanol to precipitate protein, extracted with chloroform, and an aliquot of the aqueous layer lyophilized, dissolved in water, and assayed by HPLC with UV detection.

Statistical Analyses

Statistical analyses were carried out with SPSS 12.0. Data were represented as mean±SEM. Unpaired Student's t test, one-way analysis of variance (ANOVA), ANOVA with repeated measures, two-way ANOVA were used to assess the statistical effects, as described in detail in the context. Tukey's HSD post hoc analyses were conducted when appropriate. The significance level was set at $p<0.05$.

Results

Figure 3:
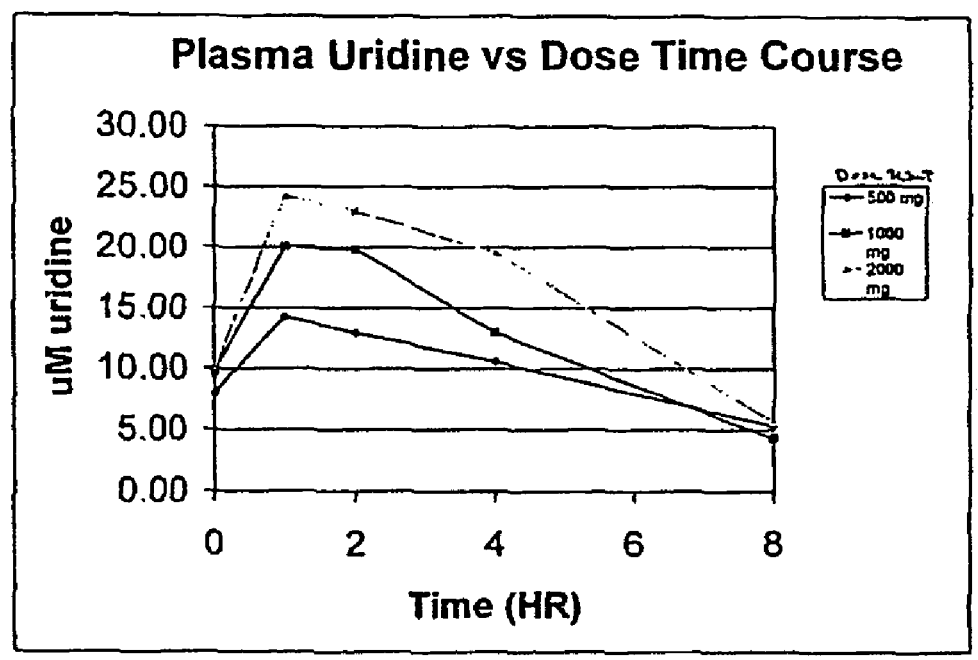
FIG. 3. Oral UMP administration raises blood uridine levels in humans. Depicted is the ratio of uridine (set as 100% value) to cytidine in plasma after oral administration of 250 milligram per kg of body weight (mg/kg) of uridine.

Subjects were administered 500, 1000, or 2000 mg UMP orally, and blood uridine levels were measured at baseline and 1, 2, 4 and 8 hours (hr) following dosing. Plasma uridine levels were assayed as described in Example 1. Plasma uridine levels increased in response to oral UMP in a dose-dependent fashion, then returned to baseline levels within 8 hr (FIG. 3).

Example 3

Oral Administration of Uridine or UMP Increases Plasma Uridine Levels in Gerbils Methods Experimental Design Groups of eight to nine male gerbils (60-80 g) were fasted overnight, administered (a) uridine (Sigma, St. Louis, Mo.; 250 mg/kg body weight) (FIG. 4) or disodium UMP (1 mmol/kg body weight, a dose equivalent to 250 mg/kg uridine by gavage) (FIG. 5) and sacrificed by decapitation under Telazol anesthesia one hour later. For FIG. 6, gerbils were fed chow (Harlan Teklad, Madison, Wis.) ad lib containing either 0.0.1, 0.5 or 2.5% UMP by weight for 4 weeks, fasted overnight, then sacrificed one hour after consumption of a last meal of the same composition. Blood collected from the neck was collected into tubes containing EDTA and was treated as described above for Example 2.

Results

Figure 4:
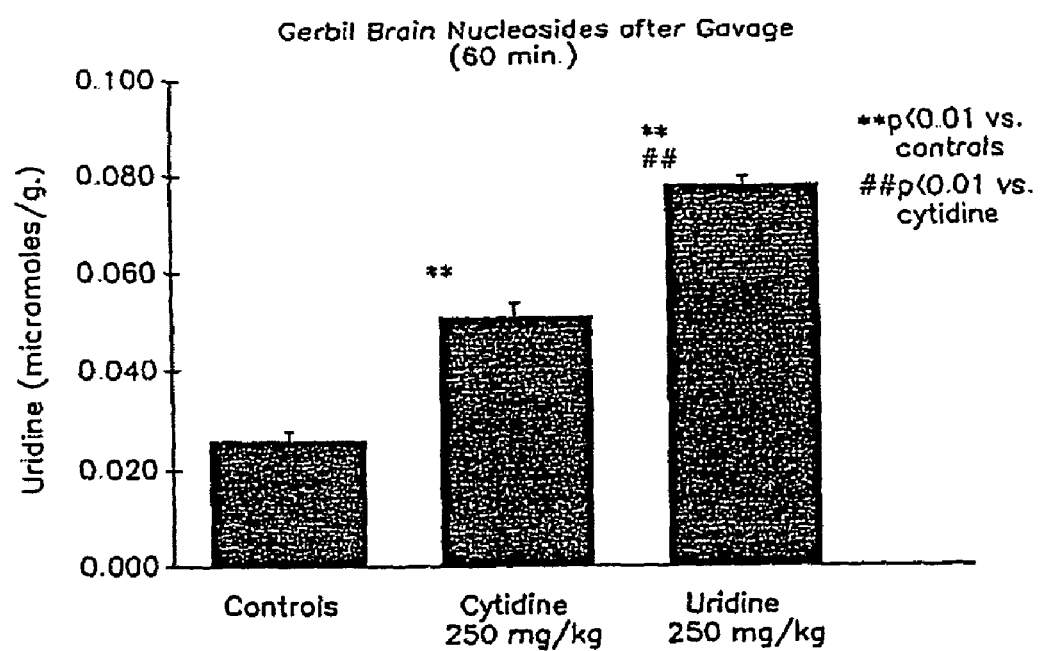
FIG. 4. Oral uridine administration raises blood uridine levels in gerbils. Depicted are plasma uridine levels 60 minutes following mock administration or administration of cytidine or uridine. **: $p<0.01$ vs. mock-fed control; ##: $p<0.01$ vs. cytidine.

To ascertain whether oral administration of uridine can raise plasma uridine levels, gerbils were fed by gavage 250 mg/kg cytidine or uridine. 60 minutes (min) later, plasma uridine levels were assessed by the method described in Example 1. Both dietary cytidine and uridine increased plasma uridine levels by a statistically significantly margin relative to a control group that was fed chow not containing cytidine or uridine, both dietary uridine resulted in plasma uridine levels approximately 3-fold higher than dietary cytidine (FIG. 4).

Figure 5:
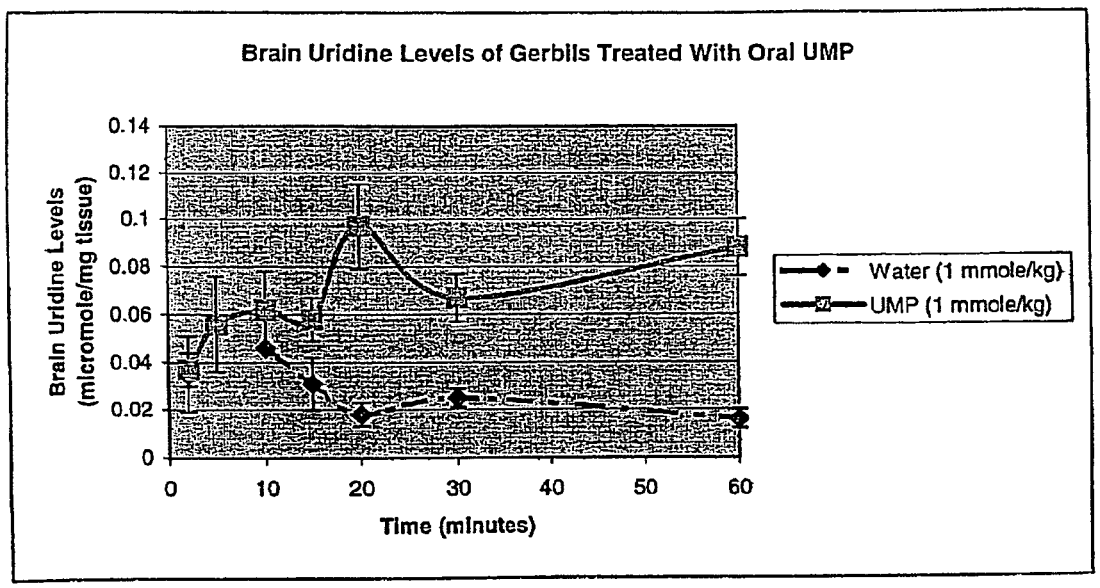
FIG. 5. Oral UMP administration raises blood uridine levels in gerbils. Depicted are plasma uridine levels at various time points following administration or administration of water or UMP.

In a separate experiment to assess the time course of the increase in plasma uridine levels, gerbils were administered either water or 1 millimole (mmol) UMP per kilogram (kg) body weight, were sacrificed at various time points in the following 60 min, and plasma uridine levels were assessed. Plasma uridine levels increased within 10 min of administration, reaching peak levels by 30 min (FIG. 5).

Figure 6:
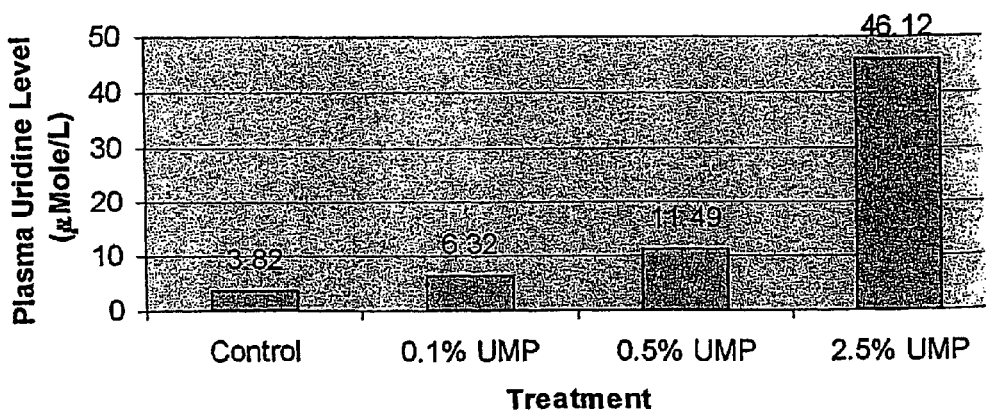
FIG. 6. A UMP-supplemented diet raises blood uridine levels in gerbils. Depicted are plasma uridine levels in gerbils fed a diet containing the indicated percentages of UMP.

In another experiment, gerbils were fed either a control diet or a diet containing 0.1%, 0.5%, or 2.5% UMP. One hour later, plasma uridine levels were assessed. As depicted in FIG. 6, plasma uridine levels increased in response to dietary UMP in a dose-dependent manner. These results indicate that orally administered uridine is absorbed into the bloodstream.

Example 4

Oral Administration of Uridine or UMP Increases Brain Uridine Levels in Gerbils Materials and Methods Gerbil Brain Tissue Preparation Brains were quickly removed from the skull after decapitation, frozen on dry ice, homogenized in 80% methanol, centrifuged, lyophilized and analyzed as described for Example 3.

Results

Figure 7:
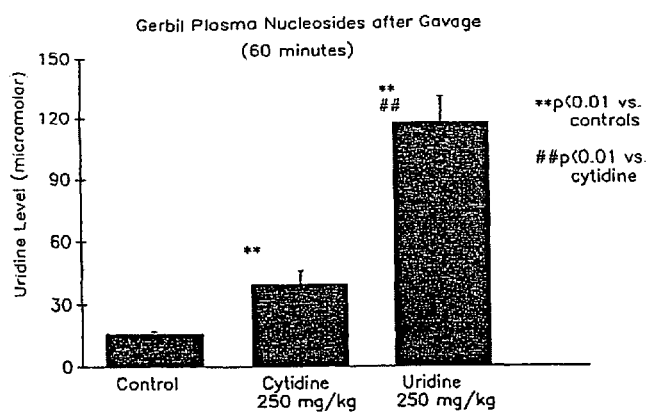
FIG. 7. Oral uridine administration raises brain uridine levels. Depicted are brain uridine levels 60 minutes following mock administration or administration of cytidine or uridine. **: $p<0.01$ vs. mock-fed control; ##: $p<0.01$ vs. cytidine.

To ascertain whether oral administration of uridine can raise brain uridine levels, brains of the gerbils from the first experiment in Example 3 were homogenized, and the uridine levels were assayed. Oral administration of cytidine resulted in a two-fold increase in brain uridine levels, and oral administration of uridine resulted in a greater than a three-fold increase in brain uridine levels, relative to the control animals (FIG. 7). All differences between groups were statistically significant.

In order to assess the time course of the increase in plasma uridine levels, brain uridine levels were assessed in the gerbils from the second experiment of Example 3. Brain uridine levels increased within 10 min of uridine administration, reaching peak levels within 30 min, similar to the results observed with plasma uridine levels (FIG. 8). These results indicate that orally administered uridine is efficiently transported into the brain.

Example 5

Uridine is Readily Converted to Cytidine in the Brain

In a separate experiment, gerbils were orally administered 250 mg/kg body weight uridine, and 60 min later plasma and brain levels of cytidine and uridine were assessed. The fold-increases relative to control animals was calculated and are depicted in FIG. 9A (plasma) and FIG. 9B (brain). In each case, the fold-increase of cytidine was normalized to the fold increase of uridine, which was arbitrarily set as 100%. These results indicate that (a) uridine in the bloodstream is transported into the brain and (b) uridine is metabolically processed differently in the brain than in plasma; specifically, it is more efficiently converted to cytidine than in plasma.

Example 6

Uridine Increases Levels of the Phospholipid Precursor CDP-Choline in the Brain and in a Neural Cell Line Methods Experimental Design Data was pooled from three experiments, with group sizes ranging from 5 to 16 animals. Male gerbils (60-80 g) were given UMP (1 mmole/kg body weight) by gavage and sacrificed at the indicated times. After brain homogenization, protein precipitation, and lyophilization as described for Example 4, samples were analyzed by HPLC-UV.

Assessment of CDP-Choline Levels

Brain tissue or cells was dissolved in methanol/chloroform (1:2 vol/vol), centrifuged, and the aqueous phase was dried under vacuum, resuspended in 100-200 μL water and separated by HPLC on an ion-exchange column (Alltech Hypersil APS-2, 5 μM, 250×4.6 mm). CDP-choline was eluted with a linear gradient of $NaH_2PO_4$ buffers A (1.75 mM $NaH_2PO_4$, pH 2.9) and B (500 mM, pH 4.5), which allowed resolution of CDP-choline from closely co-eluting substances such as UMP over 40 min. The retention time for CDP-choline was 9.5 min. Individual nucleotide peaks were detected by UV absorption at 380 nm, and were identified by comparison with the positions of authentic standards, as well as by the addition of nucleotide standards to selected samples.

PC12 cells

PC12 cells were maintained in Minimal Essential Medium (MEM; Invitrogen, Carlsbad, Calif.) supplemented with 10% fetal bovine serum (FBS) at 37° C. Experimental incubations were for 2 or 4 days in medium containing 50 ng/ml mouse 2.5 S (2.5 subunit) NGF and 1% FBS, with or without test compounds. NGF and FBS were obtained from Invitrogen.

Results

In order to assess the effect of orally administered uridine on levels of phospholipid precursors in the brain, brains of the gerbils from the second experiment of Example 3 were assayed for levels of CDP-choline, a key intermediate in phospholipid biosynthesis via the Kennedy pathway. Levels of CDP-choline rose significantly in a linear fashion (regression analysis, r=0.98, p<0.02) for 30 min after administration of UMP (FIG. 10).

To directly demonstrate conversion of uridine to CDP-choline in neural cells, PC 12 cells, a cell line capable of differentiation into neural cells, were treated with uridine, and intracellular levels of CDP-choline were measured. Uridine treatment resulted in a statistically significant increase in CDP-choline levels after 50 minutes (FIG. 11). These results suggest that, after transport to the brain, uridine is converted to phospholipid precursors such as CDP-choline, perhaps via the intermediate CTP, and therefore may possibly help augment of cognitive function by increasing synthesis of phospholipid precursors in brain cells.

Example 7

Oral Administration of UMP Increases Neurotransmitter Release in Brains of Aged Rats Methods Animals and Dietary UMP Supplementation Male middle aged Fischer 344 rats, 22-24 months old at the time of doing microdialysis, were obtained from National Institute on Aging (Harlan Sprague-Dawley, Indianapolis, Ind. Rats were housed individually under standard husbandry conditions and exposed to 12 hr light/dark cycle with food and water provided ad libitium. Each rat consumed approximately 500 mg/kg/day of UMP·2Na ($LD_{50}$ by i.p. of uridine is about 4.3 g/Kg).

Rats were acclimated to the animal facility for more than 7 days before fed a control laboratory diet (Teklad Global 16% protein rodent diet, TD.00217, Harlan Teklad, Madison, Wis., or this diet fortified with UMP·2Na$^+$ (2.5%, TD.03398, UMP·2Na$^+$; Numico Research, the Netherlands) for 6 weeks.

Rats were not fed with the research diet until at least 7 days later after their arrival. They were weighed at the time of beginning feeding (t=0), as well as 1, 2, 4, 6 weeks later. At time 0, rats were randomly assigned into two groups. There were no significant differences of body weight between groups ($F_{1,11}$=3.03, p>0.05); average weight was 455±5 (N=13 rats). Repeated measures with weeks as within-subjects factor showed feeding time (0, 1, 2, 4, 6 weeks) significantly changed body weight ($F_{4,44}$=2.65, p<0.05), while neither UMP-diet (vs. control) nor UMP×time interaction affected body weight ($F_{1,11}$=0.01, $F_{4,44}$=1.25, respectively; all p>0.05).

The experiment described in this Example was performed twice, each time with 7 control rats and 9 rats administered the UMP diet.

Chemicals and Solutions

Dopamine (DA), dihydroxyphenylacetic acid (DOPAC), homovanillic acid (HVA), serotonin (5-HT), 5-hydroxyindoleacetic acid (5-HIAA), and 3,4-dihydroxybenzoic acid (DHBA; internal standard) were purchased from Sigma (St. Louis, Mo.) and were dissolved in $HClO_4$ (0.1 M) to make 1 mM stock solutions, and aliquots were kept at −80° C. Ketamine hydrochloride (100 mg/ml) was purchased from Fort Dodge Animal Health (Fort Dorge, Iowa). Xylazine (20 mg/ml) originated from Phoenix Scientific, Inc. (St. Joseph, Mo.).

Ringer solution consisted of NaCl 147, KCl 2.7, $CaCl_2$ 1.2 and $MgCl_2$ 0.85 mM. For high potassium solution, KCl was increased to 80 mM, with NaCl decreased to 69.7 mM to maintain osmolarity. All solutions were made from doubly distilled deionized water and filtered by Steriflip® (Millipore, Bedford, Mass.).

In Vivo Microdialysis

Rats were anesthetized with a mixture of ketamine and xylazine (80 and 10 mg/Kg of body weight, respectively, intraperitoneally), and were placed in a Kopf stereotaxic frame. All surgical instruments were sterilized by a hot bead dry sterilizer or 70% ethanol. A small hole was drilled into the skull by a 2-mm trephine bone drill. CMA/11 14/04 Cupr probe (O.D. 0.24 mm, 4 mm membrane, 6,000 Da, CMA microdialysis, Sweden) was implanted into the right striatum (AP=+0.5, ML=−3.0 from Bregma, DV=−7.3 mm from Dura, as described in Paxinos G et al, The Rat Brain in Stereotaxic Coordinates, 2$^{nd}$ ed., Academic Press, San Diego) with incisor bar set at −5.0 mm. Probes were secured permanently in position using dental cement and three anchor screws to the skull. After surgery, rats were injected intraperitoneally with saline (5 ml/kg) and kept on a heating pad maintaining body temperature at 37° C. until awaking.

The freely moving rat was perfused in a circular bowl on a rotating platform obviating the need for a liquid swivel (see Wang L et al, Neurochem Int 42: 465-70, 2003), and was habituated to the environment on the first day after surgery. Experiments were performed approximately 48 hr after the surgery, and were carried out between 10:00 am to 4:00 pm. Ringer's solution was perfused continuously using Fluorinatedethylenepropylene (FEP) Resin tubing and a gas-tight syringe (Exmire type I, CMA), at a constant rate of 1.5 µl/min by a microinfusion pump (CMA/100). Dialysates were collected at 15-min intervals. 5 µl of antioxidant mixture, consisting of 0.2 M $HClO_4$ and 0.1 mM EDTA, was added to the sampling vial prior to collection to protect dopamine and its metabolites. The samples within the first 60 min were discarded from analysis. Subsequently, 3 consecutive sessions of samples were collected. Except for the last session (1.5 hrs, 6 samples), the others were collected for 1 hr (4 samples). The order was as follows: session 1 (aCSF), 2 (High $K^+$), 3 (aCSF). All samples were collected on crushed ice, instantly frozen and kept at −80° C. until HPLC analysis.

Brain Dissection for the Proteins and Monoamines

After microdialysis experiments, rats were anesthetized with ketamine and xylazine (80 and 10 mg/Kg, i.p). A black ink was pushed through the probe to stain the tissue around the probe. Rats were decapitated with a guillotine. Brains were quickly dissected on a chilled dissection board. The left striatum was snap-frozen in an Eppendorf tube placed in liquid nitrogen for future protein assays. The right striatum was further dissected and the position of probe was determined by visual observation. Data were not included if probe was found not within the striatum.

An additional group of rats (20 months old; n=6 for both control and UMP) were fed for 6 weeks. No microdialysis was carried out in these rats. Striata (both left and right) were collected as above to determine tissue levels of dopamine and its metabolites.

Extraction of Tissue Dopamine Samples

The striatum were weighed and homogenized in an Eppendorf tube on ice for 1 min with 1 ml of $H_2O$ containing 0.1 M $HClO_4$ and 1 µM EDTA. After vortexing for 10 seconds, an aliquot was used for Bicinchoninic Acid (Sigma, St. Louis, Mo.) protein assay. The homogenates were then filtered with Ultrafree-MC centrifugal filter units (Millipore, 14,000 rpm/15 min/4° C.). A 1:10 dilution was made before the aqueous layer was subjected to HPLC. DHBA was added to the samples prior to homogenization as the internal standard. Concentrations of dopamine and its metabolites were determined by HPLC, and values from the three repeated measures were averaged and normalized to the amount of protein per sample.

Analysis of Dopanime and Metabolites

DA and metabolites in dialysates and tissue samples were determined using an ESA Coulochem II 5100A detector ($E_1$=−175 mV; $E_2$=+325 mV; $E_{guard}$=350 mV) with an ESA Microdialysis Cell (model 5014B, ESA, North Chelmsford, Mass.). The mobile phase (MD-TM, ESA) consisted of 75 mM $NaH_2PO_4$, 1.7 mM 1-octanesulfonic acid, 100 µl/L Triethylamine, 25 µM EDTA, 10% acetonitrile, pH 3.0. The flow rate was 0.4 mL/min. The column (ESA MD 150, 3×150 mm, 3 µm, 120 Å) was kept in a 40° C. column oven. Samples were injected to HPLC by an Alltech 580 autosampler (Alltech, Deerfield, Ill.) and maintained to 4° C. with a cooling tray during analysis. Data were captured by Alltech AllChrom™ data system, and analyzed with AllChrom plus™ software. A timeline program, which could change the detection gain during sample separation and detection, was used to make it possible to get low DA and high metabolites concentration data in dialysate through one injection.

Data Analysis

Data were represented according to sampling time of six to nine measurements each point (means±standard error of measurement [S.E.M.]). Basal values of DA and major metabolites were determined based on the averages of the first four consecutive samples prior to $K^+$ stimulation (mean value in the dialysate was 10.2±0.4 nM, n=22), which was assigned a value of 100%. Statistics were performed using two-way ANOVA (Treatment×time) with Turkey's HSD post hoc test. One-way ANOVA was used to compare the differences among the three groups in each time point. A p value of >0.05 was used to assess statistical significance. Basal levels of dopamine were homogeneous between the two replicated experiments and were therefore pooled into the corresponding groups ($F_{1,20}$=3.99, p>0.05). Basal DA levels in the dialysates were stable after 1 hr equilibration, in the four consecutive samples prior to $K^+$ stimulation ($F_{3,57}$=0.15, p>0.05; one-way ANOVA with repeated measures using sampling time (0, 15, 30, 45 min) as within-subjects factor).

Similar to basal DA levels, basal levels of DOPAC and HVA in the dialysates were 612±14 and 369±7 nM (n=22 rats), and were stable ($F_{3,57}$=1.06, $F_{3,57}$=0.84, respectively; in each case, p>0.05). There were no effects of UMP treatment on the basal DOPAC and HVA levels (Control vs. UMP-1 week vs. UMP-6 weeks; $F_{2,19}$=0.27, $F_{2,19}$=0.03, respectively; in each case, p>0.05).

Results

In order to assess the effect of orally administered uridine metabolites on neurotransmitter release in the brain, aged rats maintained in a restricted environment consumed for 1 or 6 weeks either a control diet or a diet supplemented with 2.5% UMP. UMP supplementation did not affect basal DA levels in the dialysate among treatment groups (control vs. UMP-1 week vs. UMP-6 weeks; $F_{2,19}$=0.98). DA concentration in the dialysate was 10.2±0.4 nM (n=22 rats).

The effect of dietary UMP supplementation on $K^+$-evoked striatal DA release (following perfusion with the high-K+ solution) is depicted in FIG. 12A. A statistically significant difference ($F_{2,266}$=3.36) was found in DA levels in the dialysates among the control, UMP-1 week, and UMP-6 weeks treatment groups. Post hoc multiple comparisons revealed a significant difference between control and UMP-6 weeks' groups. Data were further divided into three sections (before, $K^+$-evoked and after), which also revealed a significant enhancement of $K^+$-evoked DA release between control and UMP-6 weeks' groups, from 283±9% to 341±21% (FIG. 12B). The UMP-1 week group also exhibited increased DA release (316±15%) relative to the control group; however, this increase was not significant.

Next, the effect of dietary UMP supplementation on the DA metabolites 3,4-dihydroxyphenylacetic acid (DOPAC) and homovanilic acid (HVA) in striatal dialysate was assessed. $K^+$-depolarization, significantly deceased DOPAC (FIG. 13A) and HVA (FIG. 13B) to 65±4% and 51±4% compared to baseline levels in all groups ($F_{2,95}$=51.90, $F_{2,95}$=92.74, respectively; all p<0.01). There were no differences in $K^+$-decreased DOPAC and HVA levels among treatment groups ($F_{2,266}$=1.01, $F_{2,266}$=1.20, respectively). Changing the solution from high $K^+$ back to normal Ringer's solution at 105 min increased both DOPAC and HVA levels in the dialysate, with maximum levels attained at 30 min after changing (DOPAC, 169±9%; HVA, 149±5%). However, no significant differences were found among the three groups.

Figure 14:
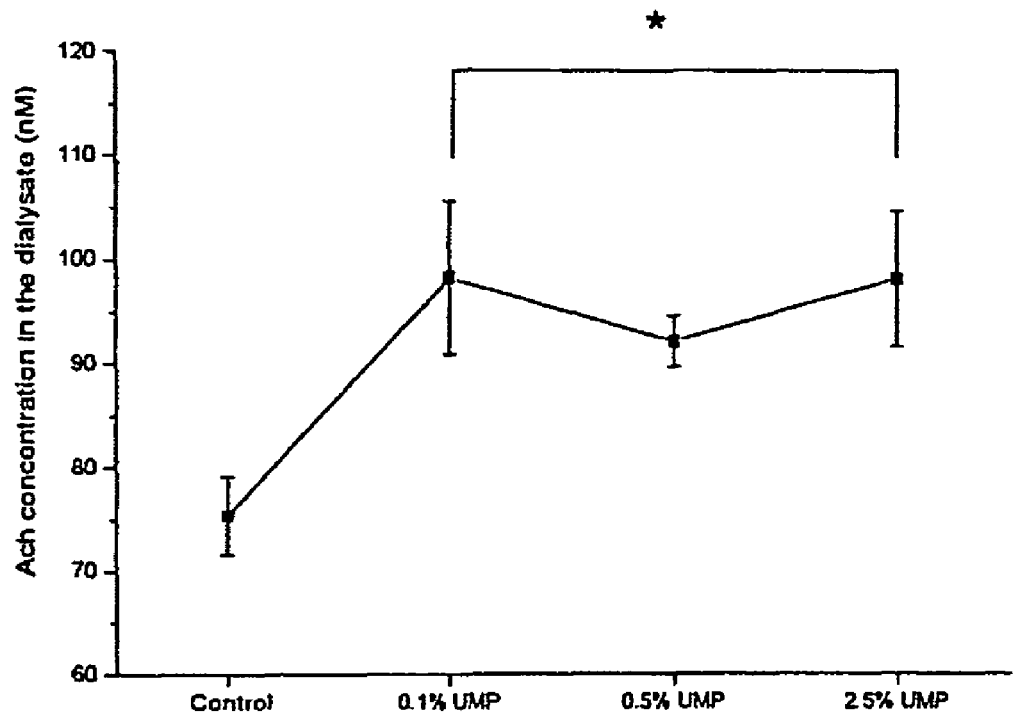
FIG. 14. Increased acetylcholine basal concentration with UMP treatment. Depicted are means+/−SEM. "*" denotes p value of $>0.05$.

In addition, dietary UMP was shown to increase the basal release of the neurotransmitter acetylcholine from neurons in the corpus striatum (FIG. 14).

These results show that (a) orally administered uridine improves neurotransmitter release in the brain; (b) uridine-mediated augmentation of brain function is a multi-species phenomenon, not limited to gerbils; and (c) augmentation of brain function by uridine occurs biologically relevant animal model for age-impaired cognitive dysfunction.

Example 8

Oral Administration of UTP Increases Levels of NH-70 and NF-M in Brains of Aged Rats Methods Data Analysis Data were represented according to UMP treatment of six to sixteen measurements each group (means±S.E.M.). One-way ANOVA with Turkey's HSD post hoc tests were used to compare the difference among the treatments the Newman-Keuls multiple range test was used for the data in FIG. 16.

Western Blotting

Striatal tissues were placed in Eppendorf tubes containing 200 µl lysis buffer (60 mM Tris-HCl, 4% SDS, 20% glycerol, 1 mM dithiothreitol, 1 mM AEBSF, 8 µM aprotinin, 500 µM bestatin, 15 µM E64, 200 µM leupeptin, 10 µM pepstatin A). The samples were sonicated, boiled (10 min), and centrifuged (14,000 g for 1 min at room temperature). The supernatant fluid was transferred to a clean tube, and total protein content was determined using the Bicinchoninic Acid assay (Sigma, St. Louis, Mo.).

Equal amounts of protein (40 µg protein/lane) were loaded for sodium dodecyl sulfate-polyacrylamide gel electrophoresis (4-15% SDS PAGE; Bio-Rad, Hercules, Calif.). Prior to gel electrophoresis, bromphenol blue solution (0.07%) was added to each sample. Proteins were separated, transferred onto polyvinylidene difluoride (PVDF) membranes (Immobilon-P, Millipore), and blocked with 5% bovine serum albumin (Tris-buffered saline/0.15% Tween 20) for 1 h. After 3 10 min rinses in Tris-buffered saline (TBST), blots were incubated in TBST with various antibodies against the proteins of interest, including NH-70, NF-M (1:2000, 1:5000, respectively; Calbiochem, La Jolla, Calif.) at 4° C. overnight on an orbital shaker. Protein-antibody complexes were detected and visualized using the ECL system (Amersham, Piscataway, N.J.) and Kodak X-AR film, respectively, as suggested by the manufacturer. Films were digitized using a Supervista S-12 scanner with a transparency adapter (UMAX Technologies, Freemont, Calif.). Analysis was performed using the public domain NIH Image program (NIH V.1.61).

Results

Figure 15:
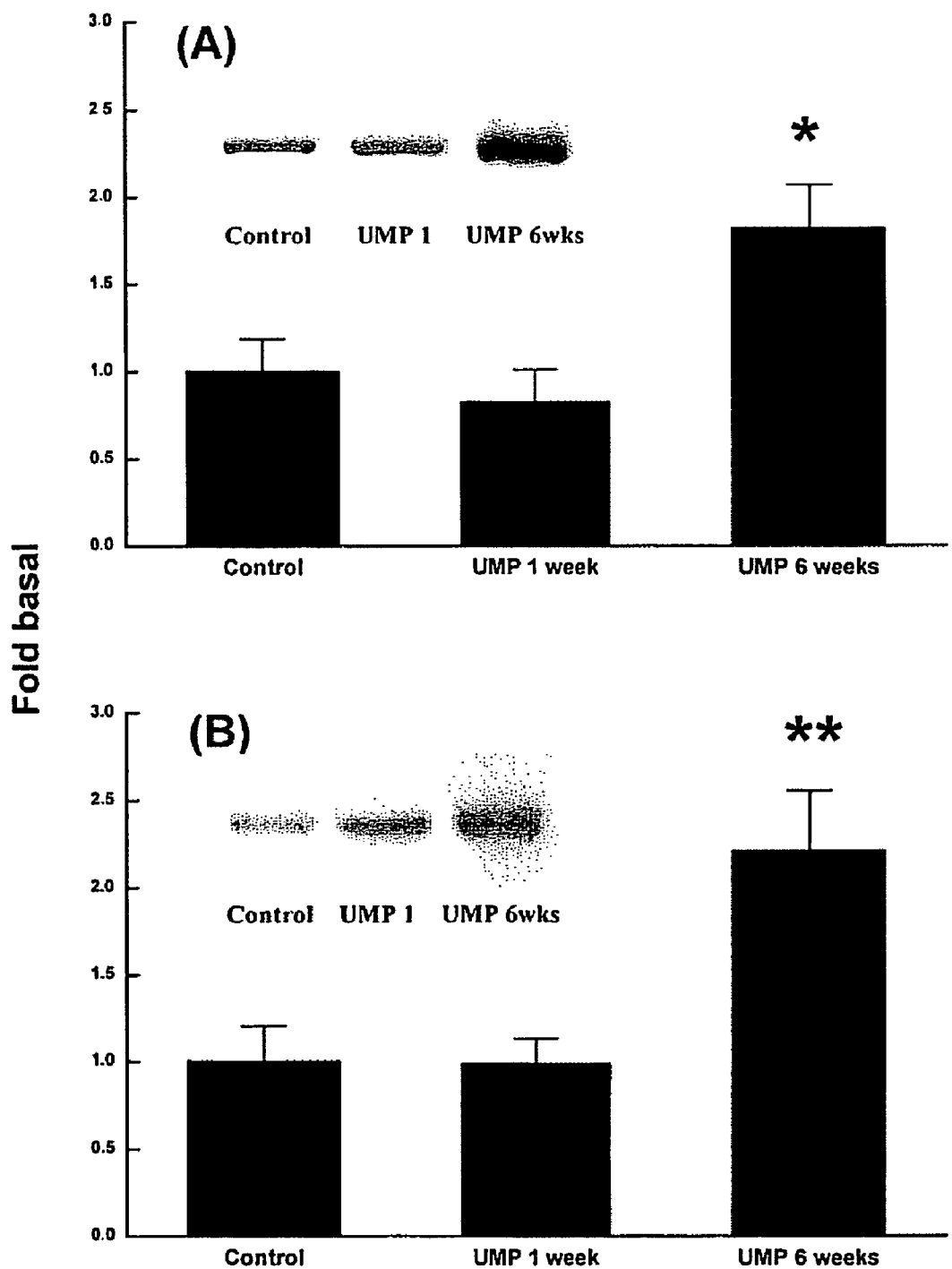
FIG. 15. Effect of UMP dietary supplemention on neurofilament protein levels in contralateral striatum. (A): NF-70. (B): NF-M*: $p<0.05$, **: $p<0.01$ compared to corresponding controls.
Figure 16:
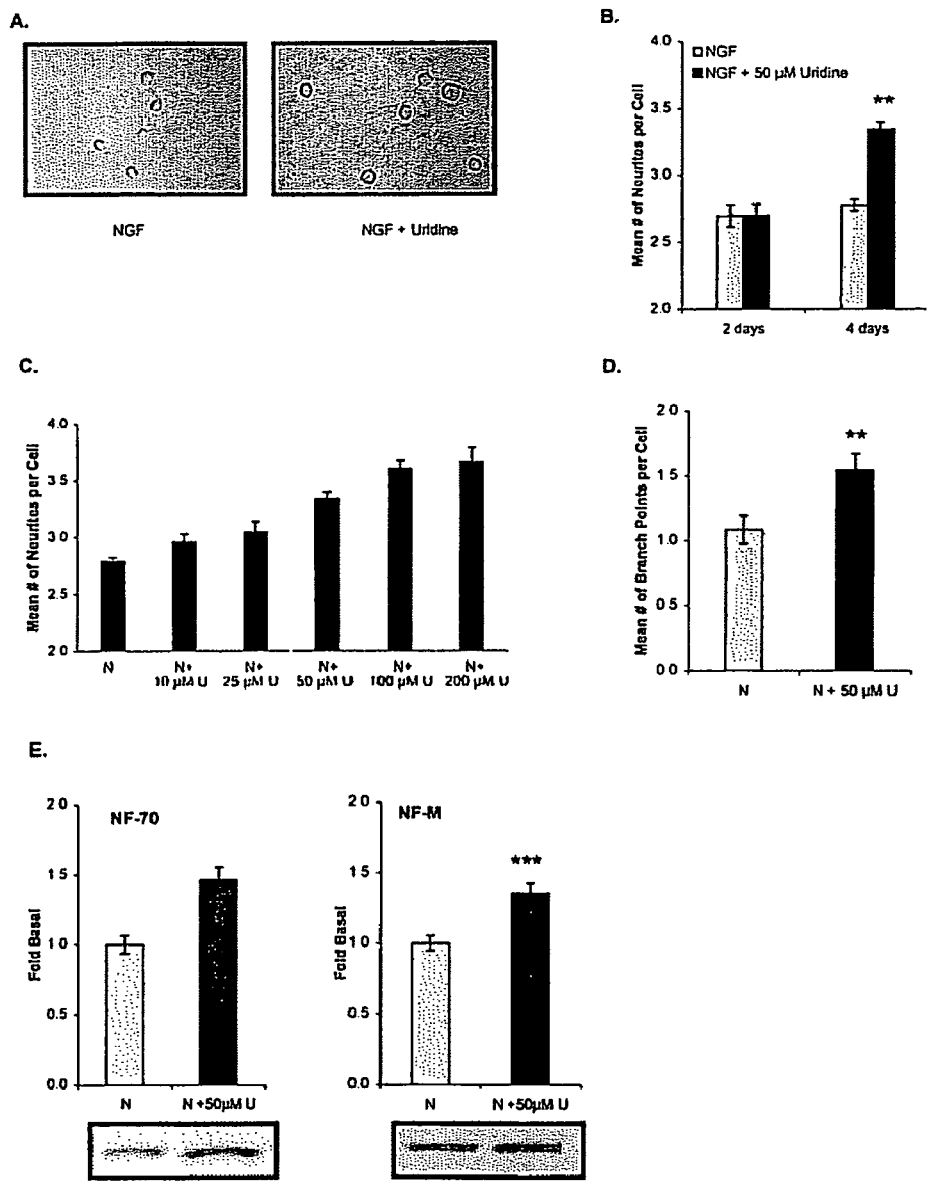
FIG. 16. Uridine treatment enhanced neurite outgrowth in PC 12 cells. A PC 12 cells treated for 4 days with NGF (50 ng/ml) in the presence or absence of uridine (50 μM). B. Number of neurites per cell after 2 or 4 days of treatment. C. Number of neurites per cell after 2 or 4 days of NGF plus different concentrations of uridine (50, 100 and 200 μM). D. Quantification of the number of branch points for each cell. E. Levels of the structural proteins NH-70 and NF-M, as determined using Western blotting. N=NGF, U=Uridine. Values represent means+SEM. : $p<0.01$, *: $p<0.001$ vs. NGF treatment.
Figure 17:
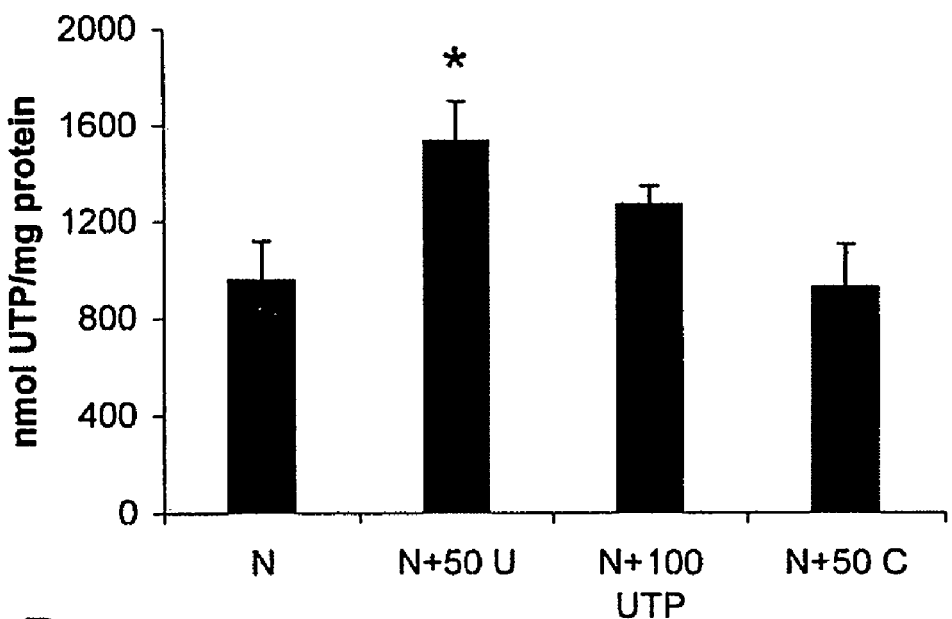
FIG. 17. Uridine treatment increased intracellular levels of UTP and CTP in PC 12 cells exposed to NGF for 2 days. Uridine treatment (50 μM) significantly increased intracellular UTP levels (A) and intracellular CTP levels (B). N=NGF, U=Uridine, C=Cytidine. Values represent means+SEM. *: $p<0.05$ vs. NGF treatment.
Figure 17:
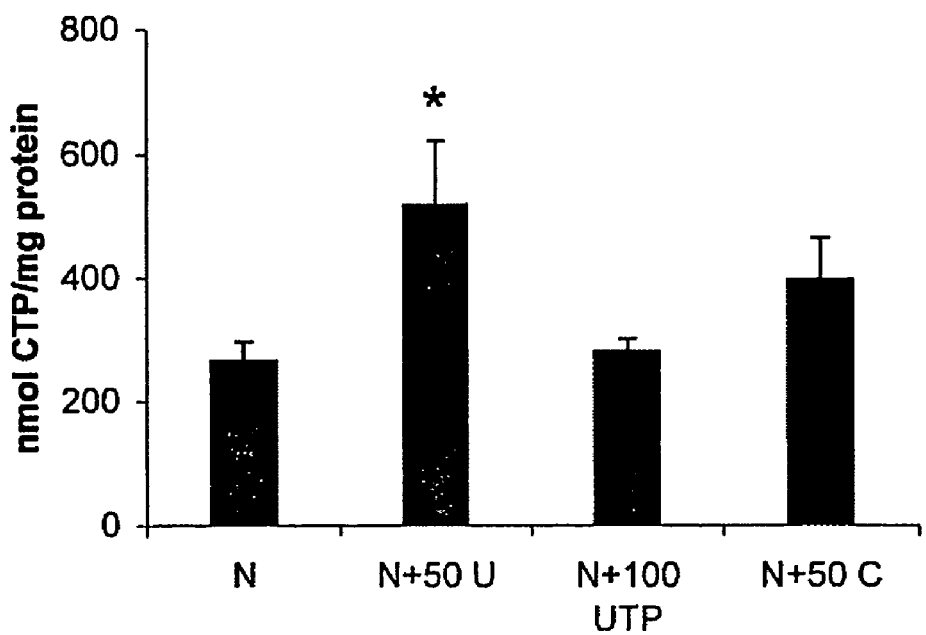
Figure 18:
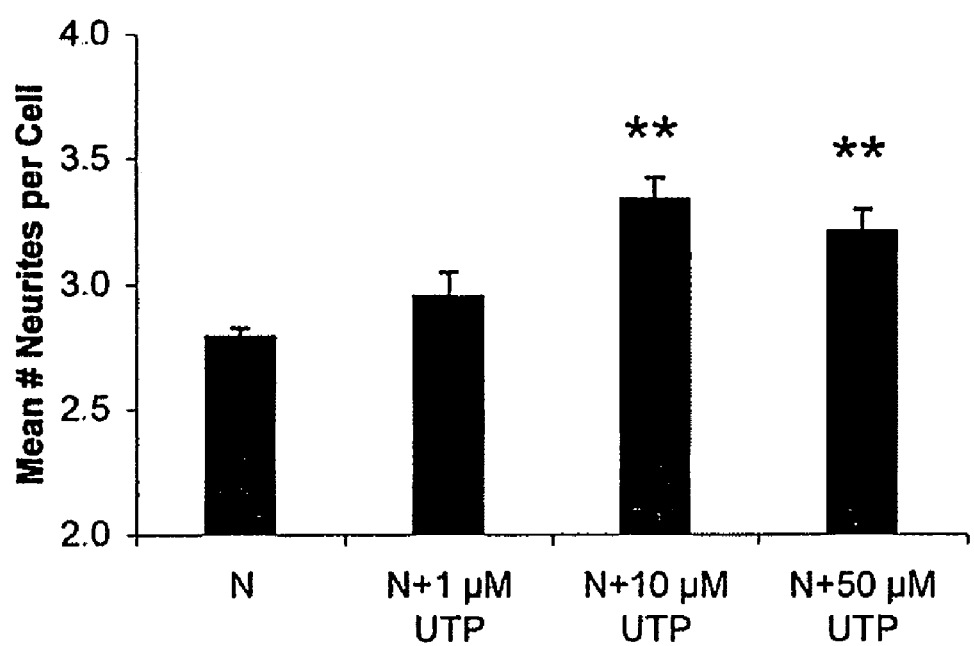
FIG. 18. UTP treatment increased neurite outgrowth. Treatment of PC 12 cells for 4 days with NGF and UTP significantly enhanced the number of neurites produced per cell, compared to treatment with NGF alone. Values represent means+SEM. **$p<0.01$.

In order to assess whether increasing uridine levels can augment the production of new membrane in the brain, levels of neurofilament-70 (NH-70) and neurofilament-M (NF-M), biomarkers of neurite outgrowth, were assessed in the brains of the rats from the experiment described in Example 7. As shown in FIG. 15, UMP dietary supplementation for 6 weeks significantly increased the levels of NH-70 (FIG. 15A) and NF-M (FIG. 15B), to 182±25% (F2,31=6.01, $p<0.05$) and 221±34% (F2,21=8.86, $p<0.01$) of control values, respectively. Consumption of a UMP diet for 1 week did not increase the levels of these two proteins compared to control group in a statistically significant manner. Levels of NH-70 and NF-M in striatum increased to 204±36% and 221±34% of control values, respectively.

Example 9

Oral Administration of Uridine or UTP Increases Neurite Outgrowth and Branching and Levels of NH-70 and NF-M in PC 12 Cells Methods Data Analysis Data are presented as mean+/−S.E.M. Analysis of variance (ANOVA) was used to determine differences between groups (significance level, $p<0.05$). When differences were detected, means were separated using the Newman-Keuls multiple range test.

Neurite Outgrowth Studies

PC12 cells were sparsely plated on collagen-coated 60 mm culture dishes in MEM containing 1% fetal bovine serum. Experimental groups were as follows: uridine, uridine triphosphate, cytidine, reactive blue 2, suramin and PPADS (Sigma, St. Louis, Mo.). All treatments were performed 24 h after plating. At the end of the treatment period, images were obtained with a phase-contrast Zeiss Axioplan 2 microscope, using OpenLab software. Six digital images were captured for each dish, for a total of 18 to 24 images per treatment group. Approximately 300 cells were quantified for each treatment group for each experiment. Experiments were performed in triplicate. Quantification of neurites, including neurite branching and neurite length, was performed by one more researchers blinded to experimental groups. Neurite length was measured using the public domain NIH software "Image J." Processes longer than the diameter of the cell body were counted as neurites. Only process-bearing cells were analyzed.

Detection of Intracellular UTP and CTP

Levels of intracellular UTP and CTP were analyzed by HPLC as described for Example 6, except that 5 mM $NaH_2PO_4$, pH 2.65 was used as buffer A.

Results

The effects of uridine treatment (10-200 µM) on NGF-induced neurite outgrowth were next tested. In the absence of NGF, PC12 cells did not sprout neurites (fewer than 1%). Uridine treatment (50 µM, 2 or 4 days) in the absence of NGF did not result in the production of neurites. In the presence of NGF, uridine (50-200 µM) significantly ($p<0.01$ or 0.001) enhanced the number of neurites per cell after 4 days of treatment (FIGS. 16A-C), whereas 2-day treatment or lower uridine concentrations (10, 25 µM) had no effect. Treatment of the NGF-exposed cells with cytidine also had no effect on neurite outgrowth.

Since uridine increased the number of neurites per cell, the effect of uridine on neurite branching and length in the presence of NGF was also assessed. After 4 days of treatment with uridine (50 µM) and NGF, the numbers of neurite branch points per cell were significantly ($p<0.01$) increased, compared with those in cells treated with only NGF (FIG. 16D). Uridine did not significantly affect average neurite length in NGF-differentiated cells.

Neurofilament proteins are highly enriched within neurites; therefore, an increase in neurite number should be associated with increased expression of neurofilament proteins.

NH-70 (70 kD) and NF-M (145 kD) levels following 4-day treatment of PC 12 cells with NGF alone, or NGF plus uridine (50 µM) were thus measured (FIG. 16E). Both NH-70 and NF-M expression significantly ($p<0.01$, $p<0.001$, respectively) increased following uridine treatment, compared to cells treated only with NGF. In the absence of NGF, uridine treatment had no effect on levels of either neurofilament protein. Thus, uridine augments neurite outgrowth in PC 12 cells.

In the absence of NGF, the addition of exogenous uridine increases intracellular UTP and CDP-choline levels in PC12 cells (Example 6). To determine whether uridine affects UTP or CTP levels in the presence of NGF, levels of UTP and CTP were measured in PC12 cells for 2 days with NGF, treated with no nucleotide, (control), uridine, cytidine or UTP, in the presence of NGF. Uridine (50 µM) significantly ($p<0.05$) increased both UTP and CTP levels (FIGS. 17A-B, respectively) compared to cells receiving only NGF treatment. UTP (100 µM) or cytidine (50 µM) did not significantly affect the intracellular levels of either nucleotide.

In order to ascertain whether UTP may mediate the effect of uridine on neurite outgrowth, PC12 cells were treated with NGF and various doses of UTP. After 4 days of treatment, UTP (10 and 50 µM) significantly ($p<0.01$) enhanced neurite outgrowth, compared to that in cells treated only with NGF. Thus, either uridine or UTP augments neurite outgrowth.

In conclusion, uridine or UTP dietary supplementation increased the levels of two major neurofilament proteins in rat brain, and was directly shown to induce neurite outgrowth in PC 12 cells.

Example 10

NGF-Differentiated PC 12 Cells Express Pyrimidine-Sensitive P2Y2, P2Y4 and P2Y6 Receptors Methods Detection of P2Y Receptors Western blots were performed as described for Example 8, using rabbit anti-P2Y2, anti-P2Y4 (both from Calbiochem); or rabbit anti-P2Y6 (Novus Biologicals, Littleton, Colo.).
Immunocytochemistry PC12 cells were treated as described above, except they were grown on 12 mm glass cover slips (A. Daigger & Co., Vernon Hills, Ill.) coated with collagen. Proteins were visualized using immunofluorescence. Briefly, the cells were fixed with 4% parafornaldehyde, permeabilized with 0.25% Triton X-100, blocked in 10% normal goat serum, and incubated overnight in the appropriate antibodies (mouse anti-NF-70, and either rabbit anti-P2Y2, rabbit anti-P2Y4 or rabbit anti-P2Y6). For P2Y2 and P2Y4 visualization, control cultures were incubated with primary antibody plus a control antigen in order to ensure that the immuno-staining would be specific. Control antigen was not available for the P2Y6 receptor. Cells were then incubated in fluorochrome-conjugated secondary antibodies for 1 hour (goat anti-rabbit ALEXA 488 and goat anti-mouse ALEXA 568; Molecular Probes, Eugene, Oreg.) and mounted on glass slides with mounting media with or without DAPI (Vector Laboratories, Burlingame, Calif.). Control antigens provided with the primary antibodies were used to ensure that immuno-staining was specific. Digital images were obtained on a Zeiss (Oberkochen, Germany) Axioplan microscope with Open-Lab software, using a Zeiss Plan-Neofluor 40× oil-immersion objective.

Results

Figure 19:
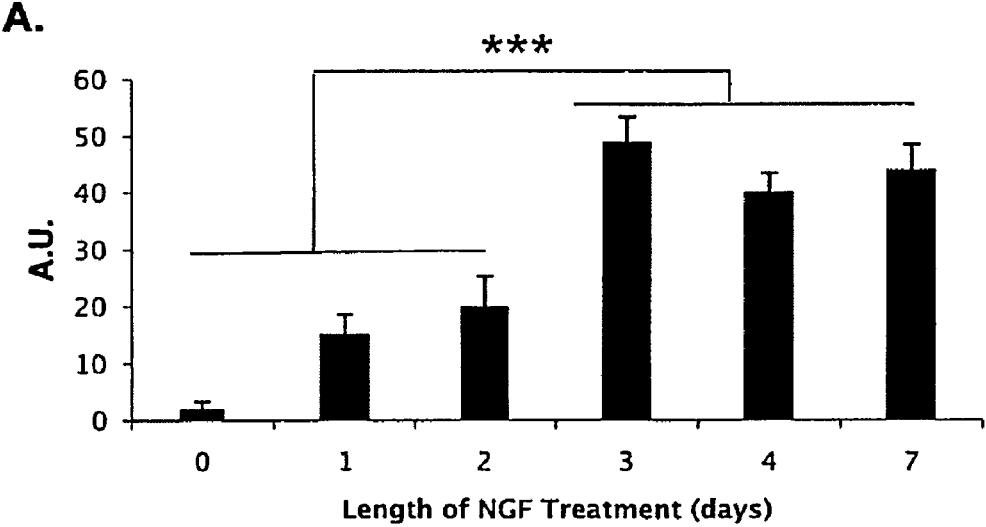
FIG. 19. NGF-differentiated PC 12 cells express pyrimidine-sensitive P2Y receptors. A. Levels of P2Y2, P2Y4 and P2Y6 receptor expression after incubation of cells with NGF for varying lengths of time. B. Following 4 days of NGF treatment, cells were fixed and NH-70 (red) and P2Y receptor (green) proteins were visualized using immunofluorescence. Left panel: P2Y2. Middle panel: P2Y4. Right panel: P2Y6 Values represent means+SEM. ***$p<0.001$.
Figure 19:
Figure 20:
FIG. 20. P2Y2 receptor co-localizes with the neuronal marker MAP-2. Left panel: P2Y2 receptor. Middle panel: MAP-2. Right Panel: Merge.
Figure 20:
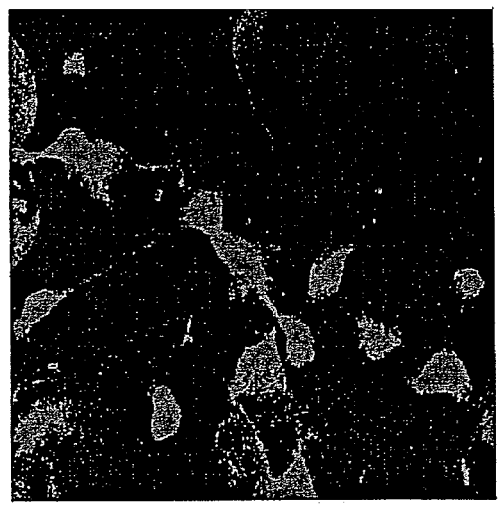
Figure 20:
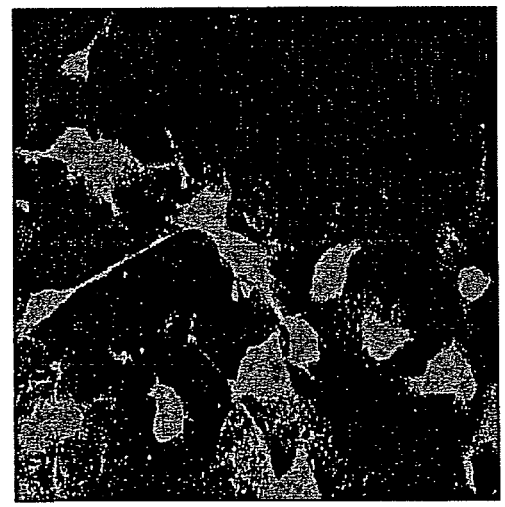

UTP is an agonist of the pyrimidine-activated class of P2Y receptors, namely P2Y2, P2Y4 and P2Y6 receptors. To determine whether these receptors participate in the mechanism by which extracellular UTP affects neurite outgrowth, it was first determined whether the receptors are expressed in PC12 cells, and whether exposure to NGF alters their expression, PC 12 cells were treated for 0-7 days with NGF and levels of the receptors measured After 3 days of NGF treatment, expression of the P2Y2 receptor reached maximal levels, which were significantly ($p<0.001$) higher than those seen at less than 3 days of NGF treatment (FIG. 19A). To visualize the expression and localization of the P2Y2, as well as the P2Y4 and P2Y6, receptors, cells were grown in the presence or absence of NGF for 4 days and then immuno-stained them for the neuritic marker NH-70, and for P2Y2, P2Y4, or P2Y6 (FIG. 19B, left to right, respectively). All three receptors were highly expressed in NGF-differentiated PC12 cells. In addition, P2Y2 co-localized with the neuronal marker MAP-2 (FIG. 20). In the absence of NGF, receptor protein expression was undetectable by immuno-staining. Moreover, the presence of uridine did not affect the expression of the receptors compared with the quantities present in cells exposed to NGF alone. Thus, the P2Y2, P2Y4 and P2Y6 receptors are present in neural cells, but not in their precursors.

Example 11

Antagonism of P2Y Receptors Inhibited the Effect of Uridine on NGF-Induced Neurite Outgrowth To ascertain whether signaling by P2Y receptors mediate induction of neurite outgrowth by uridine, PC 12 cells were incubated for 4 days with NGF, widine (100 µM) and the P2Y receptor antagonists suramin (30 µM), pyridoxal-phosphate-6-azophenyl-2',4' disulfonic acid (PPADS; 30 µM) and reactive blue 2 (RB-2; 10 µM). Each of the antagonists significantly ($p<0.05$ or $0.001$) blocked uridine enhancement of NGF-stimulated neurite outgrowth (FIG. 21). None of the P2Y receptor antagonists inhibited the uptake of uridine into the PC12 cells. These results show that signaling via P2Y receptors mediates uridine induction of neurite outgrowth.

Example 12

Phosphatidylinositol (IP) Signaling is Stimulated by UTP and Uridine

Methods

Metabolic Labeling and PI Turnover Analysis

Analysis of PI turnover was performed as described by (Nitsch R M et al, J Neurochem 69: 704-12, 1997). Briefly, cells were labeled metabolically for 36 h with 1.25 microCurie (µCi)/dish of myo-[2-$^3$H]inositol (17.0 curie/mmol; Amersham Biosciences) in serum-free MEM, washed twice with Hank's balanced salt solution (HBSS), and treated for 15 min with 10 mM lithium chloride in HBSS. Drugs were added in the presence of 10 mM lithium for 60 min at 37° C. Cells were lysed with ice-cold methanol, and lipids were removed by extraction with chloroform/methanol/water (2:2:1 by volume). Labeled water-soluble inositol phosphates were separated from free [³H]inositol by ion-exchange chromatography, using AG 1-X8 columns (Bio-Rad), and 1M ammonium formate and 0.1M formic acid as eluent Radioactivity was quantified by liquid scintillation spectrometry.

Results

P2Y2, P2Y4 and P2Y6 receptors activate the phospholipase C/diacylglycerol/inositol triphosphate (PLC/DAG/IP3) signaling pathway. To determine whether concentrations of uridine or UTP that promote neurite outgrowth activate these receptors, NGF-differentiated PC 12 cells were labeled with [3H]-inositol (50 µM) or UTP (10, 100 µM) for 1 hour, and IP signaling was assessed by measuring turnover of radio-labeled IP (FIG. 22). Formation of IP was significantly increased by addition of 100 µM UTP (p<0.05) and by 50 µM uridine (p<0.01). The P2Y receptor antagonist PPADS (100 µM) significantly (p<0.05) blocked the stimulation of IP signaling by UTP. These findings indicate that UTP promotes neurite outgrowth via P2Y receptors-mediated stimulation of the IP signaling pathway.

The findings of Examples 10-12 provide a mechanism by which uridine and its metabolites stimulate neurite outgrowth: namely, by activation of P2Y receptors. At least part of the action of the P2Y receptors is mediated by IP signaling. Taken together, the findings from Examples 7-12 provide further evidence that uridine treatment can improve cognitive function by enhancing neurotransmission by multiple mechanisms: (1) enhancing neurotransmitter release; (2) acting, through CTP, as a precursor for membrane phosphatides; (3) activating, through UTP, the P2Y receptor-coupled intracellular signaling pathway. Mechanisms (2) and (3) may act together to increase neurite formation.

Example 13

UMP-Supplemented Diets Enhance Learning and Memory in Multiple Species

Methods

Morris Water Maze

Aging rats (18 months, 500 g) were fed a control diet or a diet containing 2.5% UMP diets for six weeks. They were then shown a hidden platform in a six-foot diameter pool of water, placed somewhere in each of the four quadrants of the pool in turn, and were allowed 90 seconds in each trial to attempt to relocate the platform by swimming, and the swimming time "mean escape latency" recorded. The set of four trials was repeated on each of four consecutive days. The platform was in the same place each day. This test, known as the Morris water maze, is an indicator of spatial memory.

Food Pellet Learning Assay

Male young adult gerbils fed control or UMP-containing chow (0, 0.1, 0.5 or 2.5%) ad lib for three weeks were tested in a radial arm maze, consisting of a central chamber with four branches primed with a small food pellet at the end of each. Before testing, animals were fasted overnight; each animal was then placed in the central chamber and allowed up to 180 seconds to find all of the pellets. A shorter time required to find the pellets is indicative of improved learning and spatial memory.

Working Memory and Reference Memory Assay

Groups of ten gerbils fed control or 0.1% UMP diet for four weeks and trained to successfully find all of the food pellets as described above were then given a modified test, in which only two arms of the maze (but always the same two) contained food pellet rewards. In this test, a working memory error is one in which a gerbil revisits an arm from which it has already taken the pellet that day. A reference memory error is one in which the gerbil enters an arm which never had food pellets (during the modified tests.)

Results

Previous Examples showed that orally administered uridine improves augments the ability of neural cells to function in several ways. The present Example directly shows that uridine augments cognitive function. Aging rats (18 months, 500 g) were fed a control diet or a diet containing 2.5% UMP·2Na⁺ for six weeks, and their memory was tested using the Morris water maze, an indicator of spatial memory. Rats administered the UMP·2Na⁺-fortified diet showed a statistically significant reduction in the time required to reach the location of the platform (FIG. 23), indicating that UMP enhances spatial memory.

Figure 24:
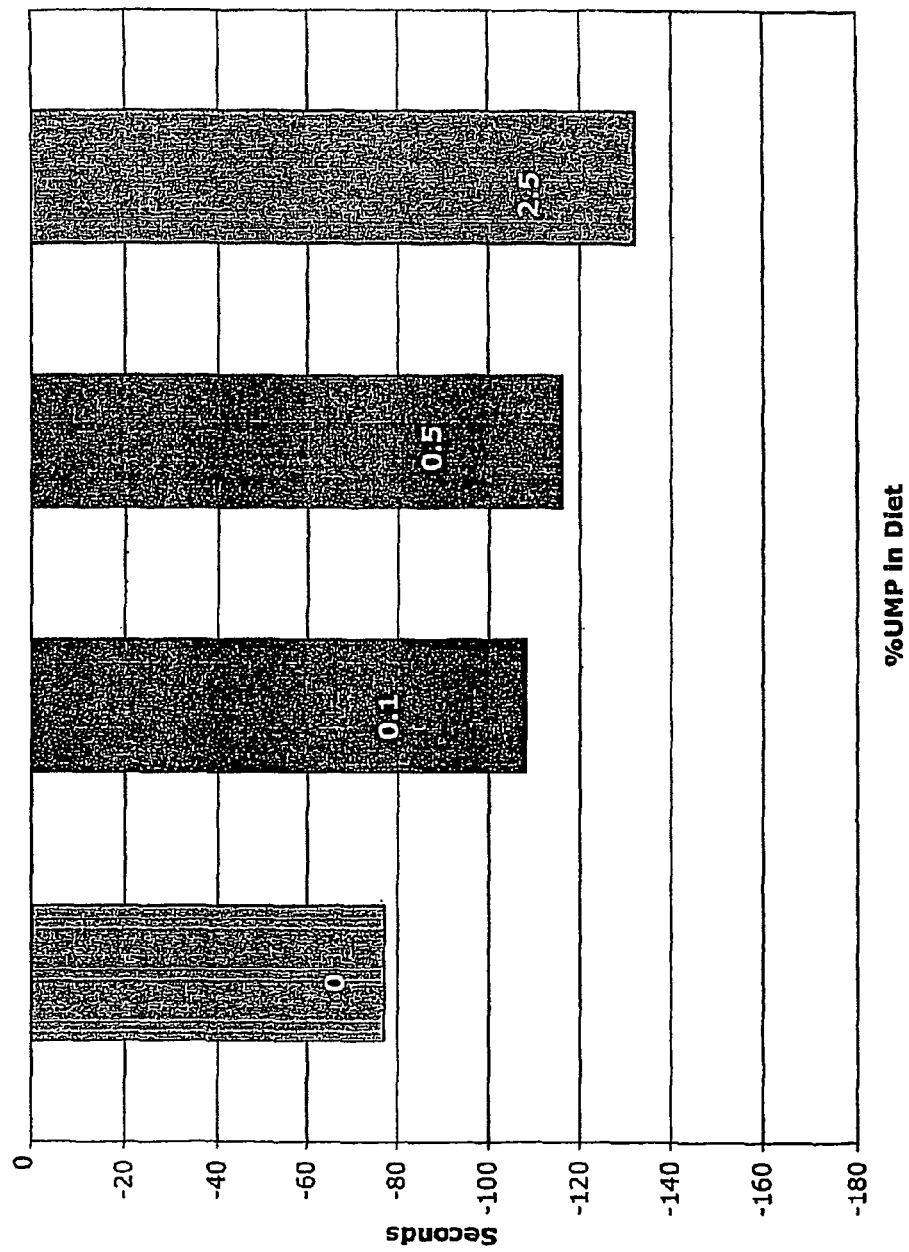
FIG. 24. Oral UMP improves learning and spatial memory in gerbils. Learning and spatial memory of gerbils fed a control diet or diets containing the indicated amount of UMP were tested in a radial arm maze. Results are depicted as the amount of time remaining before the 3-minute deadline.

The effect of orally administered uridine upon learning and spatial memory was also examined in gerbils. Male young adult gerbils fed control or UMP-containing chow (0, 0.1, 0.5 or 2.5%) ad lib for three weeks were tested in a radial arm maze, consisting of a central chamber with four branches primed with a small food pellet at the end of each. Before testing, animals were fasted overnight; each animal was then placed in the central chamber and allowed up to 180 seconds to find all of the pellets. The reduction in time needed to find the pellets requires spatial learning. UMP-supplemented diets reduced the time required for gerbils to find the pellet in a dose-dependent manner (FIG. 24).

Figure 25:
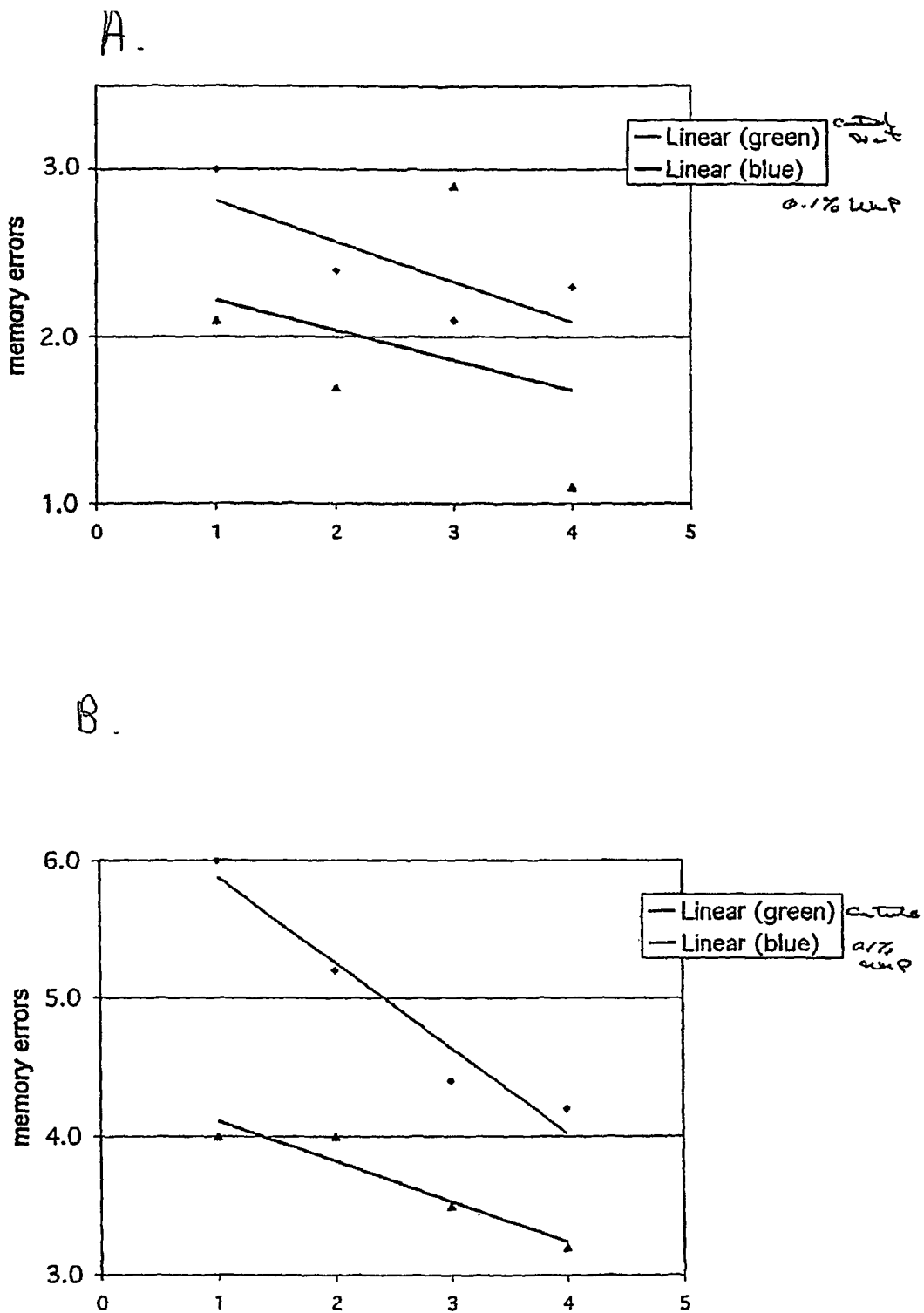
FIG. 25. Oral UMP improves working memory and reference memory. The memory of gerbils fed a control or a 0.1% UMP diet for four weeks was tested using modification of the test depicted in FIG. 24, which measured both working memory errors (A) and reference memory errors (B). Diamonds represent data points from control gerbils; triangles represent data points from gerbils fed 0.1% UMP diet.

In addition, the effect of orally administered uridine on working memory and reference memory was examined. Gerbils fed a control or a 0.1% UMP diet for four weeks and trained to successfully find all of the food pellets as described above were then given a modified test, that measures working memory and reference memory. Gerbils fed the UMP-supplemented diet exhibited reduced numbers of both working memory errors (FIG. 25A) and reference memory errors (B).

These findings directly show that (a) uridine dietary supplementation improves learning and various types (spatial, working, and reference) of memory; (b) the effect is not limited to a particular species; and (c) the effect is manifested in biologically relevant models of age-impaired cognitive function.

In summary, the findings presented herein demonstrate that orally administered uridine positively affects neurological signaling, neural cell anatomy and cognitive function. The findings also implicate several mechanisms by which uridine exerts its effects.

Example 14

Effect of Oral Uridine on Cognitive Function of Patients with Pathological Conditions Affecting Memory A clinical study is carried out with the goal of treating memory disorders and cognitive dysfunctions associated with aging, as well as memory decline and cognitive dysfunction associated with pathological conditions like Alzheimer's disease, Pick's disease, Lewy Body disease, dementias like Huntington's disease and AIDS dementia, stroke, multi-infarct dementia, minimal cognitive impairment, or age-related impairment. Patients with non-pathological dementia associated with aging are also included. Oral doses of uridine alone ranging from 5 mg to 50,000 mg are administered daily to five male and five female patients suffering from one of the diseases listed above. The adjustment in dosage to select optimally effective pharmaceutical dose is a routine procedure well known to the practitioner skilled in the relevant art.

Examples 15-26

Effect of Oral Uridine on Cognitive Function of Patients with Cognitive Dysfunction In Example 15, a clinical study is carried out, which by its design and principles is similar to clinical study of Example 14, except that patients enrolled in this study are patients with cognitive dysfunction, i.e., disorders of attention, alertness, concentration, focus, and dyslexia.

In Example 16, a clinical study is carried out, which by its design and principles is similar to clinical study of Example 14, except that patients enrolled in this study are patients with mood and emotional disorders, e.g., mania, depression, stress, panic, anxiety, insomnia, dysthymia, psychosis, seasonal effective disorders and bipolar disorders.

In Example 17, a clinical study is carried out, which by its design and principles is similar to clinical study of Example 14, except that patients enrolled in this study are patients with neurological diseases like ataxias, including Friedreich's ataxia.

In Example 18, a clinical study is carried out, which by its design and principles is similar to clinical study of Example 14, except that patients enrolled in this study are patients with movement disorders like tardive dyskinesia.

In Example 19, a clinical study is carried out, which by its design and principles is similar to clinical study of Example 14, except that patients enrolled in this study are patients with strokes, cerebral thrombosis, ischemia, and related cerebrovascular diseases resulting from hypoxia.

In Example 20, a clinical study is carried out, which by its design and principles is similar to clinical study of Example 14, except that patients enrolled in this study are patients with behavioral and neurological syndromes seen after brain trauma, spinal cord injury and/or anoxia.

In Example 21, a clinical study is carried out, which by its design and principles is similar to clinical study of Example 14, except that patients enrolled in this study are patients with diseases of the peripheral nervous system, e.g., neuromuscular disorders like myasthenia gravis, the post-polio syndrome, and muscular dystrophies.

In Example 22, a clinical study is carried out, which by its design and principles is similar to clinical study of Example 14, except that patients enrolled in this study are patients with neurological diseases associated with dopaminergic pathway, e.g., schizophrenia and Parkinson's disease and said diseases are treated by combination therapy in which uridine is one of constituents.

In Example 23, a clinical study is carried out, which by its design and principles is similar to clinical study of Example 14, except that patients enrolled in this study are patients with other diseases known in the art and involving or dependent on cholinergic or uridine/cytidine metabolic pathways.

In Example 24, a clinical study is carried out, which by its design and principles is similar to clinical study of Example 14, except that patients enrolled in this study are patients with multi-infarct dementia.

In Example 25, a clinical study is carried out, which by its design and principles is similar to clinical study of Example 14, except that patients enrolled in this study are patients with minimal cognitive impairment.

In Example 26, a clinical study is carried out, which by its design and principles is similar to clinical study of Example 14, except that patients enrolled in this study are patients with age-related impairment.

What is claimed is:

1. A method of stimulating or enhancing the production of a membrane of a brain cell or a neural cell of a subject in need thereof in the presence of NGF comprising administering to said subject between about 20 mg and about 0.75 g per day of uridine or of a uridine phosphate.

2. The method of claim 1, wherein said brain cell is newly differentiated.

3. The method of claim 1, wherein said membrane is a dendritic membrane.

4. The method of claim 1, wherein said membrane is an axonal membrane.

5. A method of stimulating or enhancing the production of a membrane of a brain cell or a neural cell in need thereof in the presence of NGF comprising contacting said brain cell with between about 20 mg and about 0.75 g per day of uridine or of a uridine phosphate.

6. The method of claim 5, wherein said brain cell is newly differentiated.

7. The method of claim 5, wherein said membrane is a dendritic membrane.

8. The method of claim 5, wherein said membrane is an axonal membrane.

9. The method of claim 1, wherein said uridine phosphate is uridine-5'-monophosphate (UMP), uridine-5'-diphosphate (UDP), uridine-5'-triphosphate (UTP), or is a salt of said UMP, UDP, or UTP.

10. The method of claim 5, wherein said uridine phosphate is uridine-5'-monophosphate (UMP), uridine-5'-diphosphate (UDP), uridine-5'-triphosphate (UTP), or is a salt of said UMP, UDP, or UTP.

* * * * *